(12) United States Patent
Yao et al.

(10) Patent No.: US 8,512,732 B2
(45) Date of Patent: Aug. 20, 2013

(54) METHOD FOR PRODUCING BIOACTIVE COMPOSITES

(75) Inventors: Takeshi Yao, Kyoto (JP); Mitsuhiro Hibino, Kyoto (JP); Takeshi Yabutsuka, Kyoto (JP)

(73) Assignee: Kyoto University, Kyoto-shi (JP)

( * ) Notice: Subject to any disclaimer, the term of this patent is extended or adjusted under 35 U.S.C. 154(b) by 542 days.

(21) Appl. No.: 12/305,270

(22) PCT Filed: Jun. 19, 2007

(86) PCT No.: PCT/JP2007/062301
§ 371 (c)(1),
(2), (4) Date: May 11, 2009

(87) PCT Pub. No.: WO2007/148682
PCT Pub. Date: Dec. 27, 2007

(65) Prior Publication Data
US 2009/0324673 A1    Dec. 31, 2009

(30) Foreign Application Priority Data

Jun. 19, 2006  (JP) ................................ 2006-168748

(51) Int. Cl.
*A61F 2/00* (2006.01)
*A01N 59/26* (2006.01)
*A61K 33/42* (2006.01)
*A61L 27/32* (2006.01)
*B05D 3/00* (2006.01)

(52) U.S. Cl.
USPC ........................... 424/423; 424/602; 427/2.27

(58) Field of Classification Search
USPC ...................................................... 424/423
See application file for complete search history.

(56) References Cited

U.S. PATENT DOCUMENTS

| 4,202,055 | A | * | 5/1980 | Reiner et al. | 623/23.57 |
| 5,068,122 | A | * | 11/1991 | Kokubo et al. | 427/2.1 |
| 5,811,302 | A | * | 9/1998 | Ducheyne et al. | 435/402 |
| 6,344,061 | B1 | * | 2/2002 | Leitao et al. | 623/23.5 |
| 6,419,945 | B1 | * | 7/2002 | Gresser et al. | 424/426 |
| 2003/0144669 | A1 | * | 7/2003 | Robinson | 606/90 |

FOREIGN PATENT DOCUMENTS

| JP | 62-172960 | 7/1987 |
| JP | 3-97466 | 4/1991 |
| JP | 10-287411 | 10/1998 |
| JP | 2005-111255 A1 | 4/2005 |
| WO | WO 2007/020928 A1 | 2/2007 |

OTHER PUBLICATIONS

International Search Report for International Application No. PCT/JP2007/062301 dated Sep. 18, 2007.

* cited by examiner

*Primary Examiner* — Fereydoun G Sajjadi
*Assistant Examiner* — Michael B Pallay
(74) *Attorney, Agent, or Firm* — Kratz, Quintos & Hanson, LLP

(57) ABSTRACT

An object of the present invention is to provide a method for producing bioactive composites having imparted thereto bioactivity, to thereby form and grow in vivo or in vitro a coating layer containing a calcium phosphate compound as the major component with a high adhesion strength on the surface of various types of porous substrates such as a porous shaped body comprising an organic polymer. The means for solving the problem is characterized by comprising at least (1) a step of immersing a porous substrate in a solution containing at least calcium ions and hydrogenphosphate ions, thereby distributing the solution to the inside of at least a part of the pores of the substrate, and (2) a step of depositing fine particles containing a calcium phosphate compound as the major component inside the pores into which the solution is introduced.

13 Claims, 22 Drawing Sheets

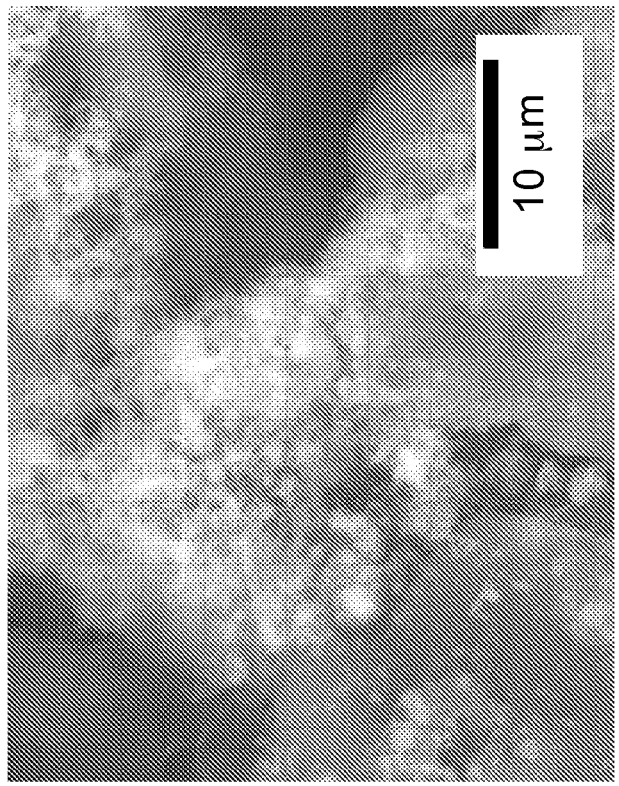
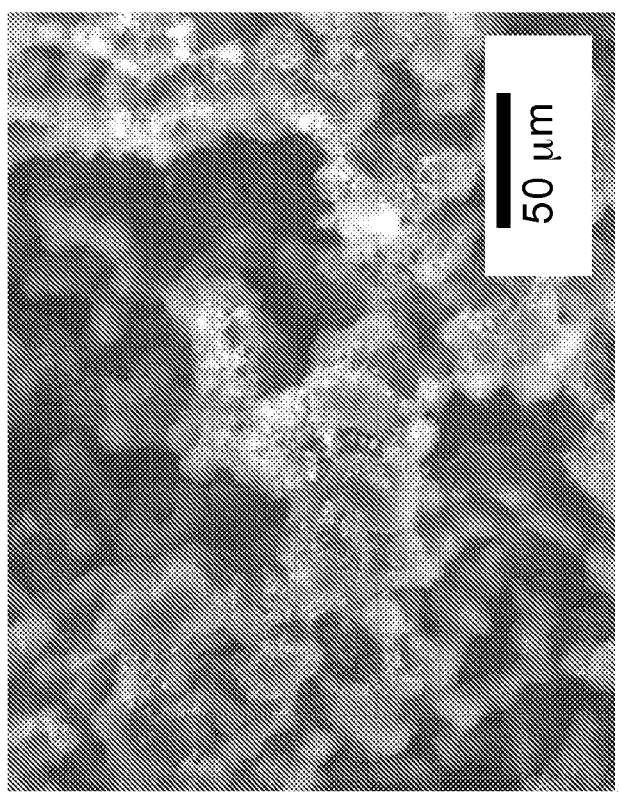
Fig.7

METHOD FOR PRODUCING BIOACTIVE COMPOSITES

TECHNICAL FIELD

The present invention relates to a method for producing bioactive composites comprising a porous substrate having bioactivity imparted thereto, which is capable of forming and growing in vivo or in vitro on the surface with a high adhesion strength, a coating layer containing a calcium phosphate compound as the major component.

BACKGROUND ART

Implants such as an artificial bone and an artificial arthrosis using porous shaped bodies comprising organic polymers as substrates are advantageous in that they have favorable biomechanical compatibility in vivo because they not only have excellent mechanical strength but also flexibility and toughness, and in that bone tissues strongly adhere to the substrate by an interlocking effect that is exerted when growing the bone tissues containing a calcium phosphate compound as the major component inside the pores of the substrate. However, in order to grow the bone tissues on the surface of the substrate, bioactivity (osteoconductive property) which induces the growth of the bone tissues should be imparted to the substrate. As the methods for imparting bioactivity to organic polymer materials known to the present include, for instance, adhering particles comprising calcium phosphate compounds on the substrate sheet and pressing, thereby embedding a part of the particles inside the sheet (Patent literature 1). Such a method, however, fails to strongly adhere the bone tissues with the substrate because the bone tissues cannot be grown inside the pores of the porous substrate.
Patent Literature 1: JP-A-2000-126280

DISCLOSURE OF THE INVENTION

Problems that the Invention is to Solve

Thus, an objective of the present invention is to provide a method for producing bioactive composites having imparted thereto bioactivity, to thereby form and grow in vivo or in vitro a coating layer containing a calcium phosphate compound as the major component with a high adhesion strength on the surface of various types of porous substrates such as a porous shaped body comprising an organic polymer.

Means for Solving the Problems

In the light of such circumstances, the present inventors intensively conducted studies, and as a result, they have found that a bioactivity can be extremely easily imparted to a substrate by a method comprising immersing a porous substrate in a simulated body fluid (SBF=Simulated Body Fluid) whose pH is adjusted to 7.0, followed by shifting the pH of the simulated body fluid to the alkaline side or immersing a porous substrate in a simulated body fluid, followed by elevating the temperature of the simulated body fluid, thereby depositing fine particles containing a calcium phosphate compound as the major component which serve as nuclei for growing bone tissues inside the pores of the substrate.

The present invention has been accomplished based on the above findings, and a method for producing bioactive composites for forming and growing a coating layer containing a calcium phosphate compound as the major component on the surface thereof is as claimed in Claim 1, which is characterized in that it at least comprises: (1) a step of immersing a porous substrate in a solution containing at least calcium ions and hydrogenphosphate ions, thereby distributing the solution to the inside of at least a part of the pores of the substrate, and (2) a step of depositing fine particles containing a calcium phosphate compound as the major component inside the pores into which the solution is introduced.

Further, the production method as claimed in Claim 2 is characterized in that, in the production method of Claim 1, the porous substrate is a porous shaped body comprising an organic polymer.

Furthermore, the production method as claimed in Claim 3 is characterized in that, in the production method of Claim 1, the average diameter of the pores is in the range of 10 nm to 1 mm.

Moreover, the production method as claimed in Claim 4 is characterized in that, in the production method of Claim 1, the porosity of the porous substrate is in the range of 10% to 65%.

Further, the production method as claimed in Claim 5 is characterized in that, in the production method of Claim 2, the organic polymer is at least one type selected from polyethylene, polypropylene, polyethylene terephthalate, polyvinyl alcohol, ethylene-vinyl alcohol copolymer, polyethersulfone, polycaprolactone, and polylactic acid.

Furthermore, the production method as claimed in Claim 6 is characterized in that, in the production method of Claim 1, the calcium phosphate compound is hydroxyapatites.

Further, the production method as claimed in Claim 7 is characterized in that, in the production method of Claim 1, the solution used in the step (1) containing at least calcium ions and hydrogenphosphate ions is such a solution which deposits fine particles containing a calcium phosphate compound as the major component by increasing the pH value.

Furthermore, the production method as claimed in Claim 8 is characterized in that, in the production method of Claim 7, the pH value of the solution is in the range of 4.0 to 7.1.

Moreover, the production method as claimed in Claim 9 is characterized in that, in the production method of Claim 1, in the step (1), a degassing treatment is carried out to thereby distribute the solution to the inside of at least a part of the pores of the substrate.

Further, the production method as claimed in Claim 10 is characterized in that, in the production method of Claim 1, in the step (1), a pressurizing treatment is carried out to thereby distribute the solution to the inside of at least a part of the pores of the substrate.

Furthermore, the production method as claimed in Claim 11 is characterized in that, in the production method of Claim 1, in the step (2), the fine particles containing a calcium phosphate compound as the major component are deposited by increasing the pH value of the solution to in the range of 7.2 to 9.0.

Further, the production method as claimed in Claim 12 is characterized in that, in the production method of Claim 11, the pH value of the solution is increased by adding a pH controlling agent having a buffer function.

Moreover, the production method as claimed in Claim 13 is characterized in that, in the production method of Claim 12, the pH controlling agent having a buffer function is tris(hydroxymethyl)aminomethane.

Furthermore, the production method as claimed in Claim 14 is characterized in that, in the production method of Claim 1, in the step (2), the fine particles containing a calcium phosphate compound as the major component are deposited by elevating the temperature of the solution.

Further, the production method as claimed in Claim 15 is characterized in that, in the production method of Claim 14, the temperature of the solution is elevated by 20° C. or more with respect to the temperature of the solution before elevating the solution temperature.

Moreover, the production method as claimed in Claim 16 is characterized in that, in the production method of Claim 1, the size of the fine particles containing a calciumphosphate compound as the major component is in the range of 1 nm to 500 µm.

Furthermore, the production method as claimed in Claim 17 is characterized in that, in the production method of Claim 1, a plasma surface treatment is applied to the porous substrate before carrying out the step (1).

Further, the production method as claimed in Claim 18 is characterized in that, in the production method of Claim 1, the porous substrate is subjected to a surface roughening treatment to provide poriform irregularities to the surface thereof.

In addition, bioactive composites according to the present invention as claimed in Claim 19, which is characterized in that it is produced by the production method of Claim 1, and fine particles containing a calcium phosphate compound as the major component are deposited inside at least a part of the pores of the porous substrate.

Additionally, according to the present invention, a method for producing bioactive composites having on the surface thereof a coating layer containing a calcium phosphate compound as the major component as claimed in Claim 20, which is characterized in that it at least comprises: (1) a step of immersing a porous substrate in a solution containing at least calcium ions and hydrogenphosphate ions, thereby distributing the solution to the inside of at least a part of the pores of the substrate, (2) a step of depositing fine particles containing a calcium phosphate compound as the major component inside the pores into which the solution is introduced, and (3) a step of forming and growing a coating layer containing a calcium phosphate compound as the major component by using the fine particles containing a calcium phosphate compound as the major component, which have deposited inside the pores, as nuclei.

Furthermore, bioactive composites according to the present invention as claimed in Claim 21, which is characterized in that it is produced by the production method of Claim 20, and a coating layer containing a calcium phosphate compound as the major component is formed and grown by using, as nuclei, fine particles containing a calcium phosphate compound as the major component, which have deposited inside at least a part of the pores of the porous substrate.

Effect of the Invention

According to the present invention, there is provided a method for producing bioactive composites having imparted thereto bioactivity, to thereby form and grow in vivo or in vitro a coating layer containing a calcium phosphate compound as the major component with a high adhesion strength on the surface of various types of porous substrates such as a porous shaped body comprising an organic polymer.

BRIEF DESCRIPTION OF THE DRAWINGS

[FIG. 7] It shows the result obtained by SEM observation of the surface of a substrate subjected to a treatment for imparting bioactivity (Sample B) in Example 3.

BEST MODE FOR CARRYING OUT THE INVENTION

Figure 1:
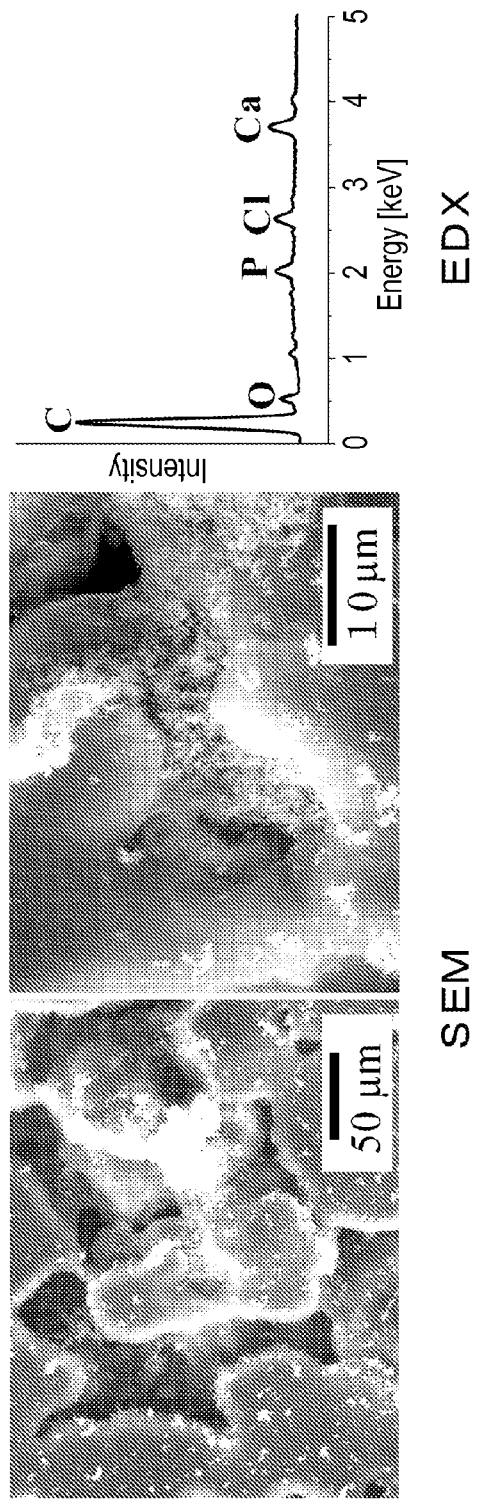
[FIG. 1] It shows the results obtained by SEM and EDX observations of the surface of a substrate subjected to a treatment for imparting bioactivity (Sample A) in Example 1.

In the present invention, a porous shaped body comprising an organic polymer can be mentioned as a representative example of a porous substrate for use as a substrate of bioactive composites. As the examples of organic polymers, included are polyethylene, polypropylene, polyethylene terephthalate, polyvinyl alcohol, ethylene-vinyl alcohol copolymer, polyethersulfone, polycaprolactone, and polylactic acid. Furthermore, the organic polymer may be a naturally occurring substance such as collagen. The porous shaped body comprising an organic polymer may be such made of a single organic polymer, or of plural kinds of organic polymers (such as polymer alloys). Furthermore, it may be a composite comprising different kinds of organic polymers. Moreover, the porous substrate is not limited to the porous shaped body comprising an organic polymer, but may be a porous shaped body comprising any material. For instance, it may be a porous shaped body comprising a metal or ceramics and the like, or may be a porous shaped body comprising a composite of an organic polymer with a metal or ceramics and the like. The shape of the substrate may be a complex shape or a simple shape, or any other shape. Specifically, the substrate may have a shape of a bone or an arthrosis, or may have a shape of joint members such as an artificial arthrosis or an artificial root. Furthermore, the shape may be plate-like, sheet-like, rod-like, or granular. The substrate having such shapes may be formed by a method according to the material. In order to form and grow in vivo or in vitro a coating layer containing a calcium phosphate compound as the major component on the surface of a porous substrate with a high adhesion strength by an interlocking effect, the average diameter of the pores is preferably in the range of 10 nm to 1 mm, and the porosity is preferably in the range of 10% to 65%. Furthermore, the porous substrate may be, in addition to foamed bodies and felt, such having surfaces with poriform irregularities provided by means of a surface roughening treatment using chemicals such as an acidic or alkaline substance, or a polishing paper, a porous coating treatment using reduced pressure plasma spraying or the like, or a grinding processing treatment such as an electrolytic in-process dressing (ELID); and, it may be a woven cloth or a non-woven cloth (the interstices among the fibers correspond to the pores).

In the method for producing bioactive composites according to the present invention, firstly, in a step (1), a porous substrate is immersed in a solution containing at least calcium ions and hydrogenphosphate ions to thereby distribute the solution to the inside of at least a part of the pores of the substrate, and then, in a step (2), fine particles containing a calcium phosphate compound as the major component are deposited inside the pores into which the solution is introduced.

The composition of the fine particles containing a calcium phosphate compound as the major component and which are deposited inside the pores is not particularly limited so long as it provides nuclei on the surface of the substrate for forming and growing a coating layer containing a calcium phosphate compound as the major component. As the calcium phosphate compounds, examples include monobasic calcium phosphate $(Ca(H_2PO_4)_2)$, dibasic calcium phosphate $(CaHPO_4)$, tribasic calcium phosphate $(Ca_3(PO_4)_2)$, tetracalcium phosphate $(Ca_4(PO_4)_2O)$, octacalcium phosphate $(Ca_8H_2(PO_4)_6)$, apatites such as hydroxyapatites, and an amorphous calcium phosphate (which may have water of crystallization). As the preferred fine particles containing a calcium phosphate compound as the major component, there can be mentioned fine particles containing hydroxyapatites as the major component. Hydroxyapatite is a compound expressed by the chemical formula $Ca_{10}(PO_4)_6(OH)_2$. Hydroxyapatites include hydroxyapatite and those derived therefrom, in which a constituent element is substituted and/or deficient. As specific examples of a hydroxyapatite whose constituent element is substituted and/or deficient, there can be mentioned hydroxyapatites whose constituent elements or groups are partly substituted by the elements of Group 1 of the periodic table, such as Na and K; or the elements of Group 2 of the periodic table, such as Mg; or the elements of Group 4 of the periodic table, such as Ti; or the elements of Group 12 of the periodic table, such as Zn; or the elements of Group 17 of the periodic table, such as F and Cl; or groups such as $CO_3^{2-}$, $HPO_4^{2-}$, $SO_4^{2-}$; or rare earth metal elements. Such elements and groups incorporated in the compound originates from the elements and groups contained in the solution that is used for depositing the fine particles. In order to obtain the fine particles that function as the nuclei having excellent biocompatibility, which effectively induce and accelerate the formation and growth of the coating layer containing a calcium phosphate compound as the major component on the surface of the substrate, the size of the particles is preferably in the range of 1 nm to 500 μm, more preferably in the range of 10 nm to 10 μm, and most preferably in the range of 50 nm to 1 μm. Further, the fine particles may be crystalline or amorphous.

As the solution for use in the step (1), which contains at least calcium ions and hydrogenphosphate ions for depositing the fine particles containing a calcium phosphate compound as the major component, there can be mentioned, for example, a solution from which fine particles containing a calcium phosphate compound as the major component deposit by increasing the pH value or by elevating the temperature; specifically, there can be exemplified a solution containing 0.02 mM to 25 mM of calcium ions and 0.01 mM to 10 mM of hydrogenphosphate ions, and whose pH value is in the range of 4.0 to 8.0. The preparation method thereof is not particularly limited, and a known preparation method can be employed. Hydrogenphosphate ions collectively mean phosphoric acid capable of generating $PO_4^{3-}$ in an aqueous solution, and included are phosphoric acid $(H_3PO_4)$, dihydrogenphosphate ion $(H_2PO_4^-)$, hydrogenphosphate ion $(HPO_4^{2-})$, phosphate ion $(PO_4^{3-})$, and condensed phosphoric acid which are generated by polymerization of two or more $PO_4^{3-}$. The concentration of calcium ions is preferably in the range of 0.2 mM to 20 mM, and more preferably in the range of 1.2 mM to 5 mM. The concentration of hydrogenphosphate ions is preferably in the range of 0.1 mM to 8 mM, and more preferably in the range of 0.5 mM to 2 mM. In order to obtain the deposits of the fine particles having excellent biocompatibility, preferred is to use a simulated body fluid (SBF: Simulated Body Fluid) as the solution for depositing the fine particles, which contains sodium ions, potassium ions, magnesium ions, chloride ions, hydrogencarbonate ions, and sulfate ions in addition to calcium ions and hydrogenphosphate ions, each at a concentration similar to the ion concentration of a human plasma. The concentration of sodium ions in the simulated body fluid is preferably in the range of 1.4 mM to 1420 mM, more preferably in the range of 14 mM to 1140 mM, and most preferably in the range of 70 mM to 290 mM. The concentration of potassium ions is preferably in the range of 0.05 mM to 50 mM, more preferably in the range of 0.5 mM to 40 mM, and most preferably in the range of 2.5 mM to 10 mM. The concentration of magnesium ions is preferably in the range of 0.01 mM to 15 mM, more preferably in the range of 0.1 mM to 12 mM, and most preferably in the range of 0.7 mM to 3 mM. The concentration of chloride ions is preferably in the range of 1.4 mM to 1500 mM, more preferably in the range of 14.5 mM to 1200 mM, and most preferably in the range of 70 mM to 300 mM. The concentration of hydrogencarbonate ions is preferably in the range of 0.04 mM to 45 mM, more preferably in the range of 0.4 mM to 36 mM, and most preferably in the range of 2 mM to 9 mM. The concentration of sulfate ions is preferably in the range of $5.0 \times 10^{-3}$ mM to 5 mM, more preferably in the range of 0.05 mM to 4 mM, and most preferably in the range of 0.2 mM to 1 mM. The simulated body fluid containing these inorganic ions at concentrations similar to the body fluid is denoted as 1.0SBF. In 1.0SBF, the concentration of sodium ions is 142.0 mM, the concentration of potassium ions is 5.0 mM, the concentration of magnesium ions is 1.5 mM, the concentration of calcium ions is 2.5 mM, the concentration of chloride ions is 147.8 mM, the concentration of hydrogencarbonate ions is 4.2 mM, the concentration of hydrogenphosphate ions is 1.0 mM, and the concentration of sulfate ions is 0.5 mM. A simulated body fluid containing the inorganic ions at a concentration x times (where x is a positive real number) higher than that of 1.0SBF is denoted as xSBF. In the present invention, it is preferred to use 0.5SBF to 5.0SBF as the solution for depositing the fine particles.

In the step (1), it is not necessary to distribute the solution for depositing the fine particles containing a calcium phosphate compound as the major component to the inside of all pores present in the substrate. However, in order to form and grow the coating layer containing a calcium phosphate compound as the major component on the surface of the substrate with a high adhesion strength by the interlocking effect, it is necessary to deposit the fine particles inside at least a part of the pores in the vicinity of the surface of the substrate, to thereby provide the nuclei for forming and growing the coating layer. In this context, it is preferred to distribute the solution for depositing the fine particles to the inside of at least a part of the pores in the vicinity of the surface of the substrate. This operation can be effectively carried out by performing a degassing treatment after immersing the substrate in the solution, thereby removing the bubbles that exist inside the pores, or by applying a pressurizing treatment using a cold isostatic pressing apparatus, thereby compressing the solution inside the pores.

The operation for depositing the fine particles containing a calcium phosphate compound as the major component from the solution in the step (2) is preferably carried out by adding in the solution a pH controlling agent having a buffer function, for instance, tris(hydroxymethyl)aminomethane or ammonia, to thereby increase the pH value of the solution. The pH value of the solution can be precisely controlled by using the pH controlling agent having a buffer function. For example, in the case the pH value of the solution for use in the step (1) is in the range of 4.0 to 7.1, the fine particles having excellent biocompatibility can be efficiently deposited inside the pores by increasing the pH value to in the range of 7.2 to 9.0. In order to assure the deposition of the fine particles, it is preferred to allow the solution in which the substrate is immersed to stand still for a predetermined duration of time after increasing the pH value of the solution, for instance, 1 hour to 30 hours. Furthermore, the solution is preferably maintained at in the range of 35° C. to 60° C. while increasing the pH value, and then allowed to stand still.

Furthermore, the operation for depositing the fine particles containing a calcium phosphate compound as the major component from the solution in the step (2) can be effected by elevating the temperature of the solution. In order to efficiently and surely deposit the fine particles having excellent biocompatibility inside the pores, preferably, the temperature of the solution is elevated by 20° C. or more with respect to the temperature of the solution before elevating the solution temperature (for example, in case the solution temperature before elevating the temperature is 40° C. or lower, the temperature is preferably elevated to 60° C. or higher).

By body implanting the bioactive composites thus produced by depositing the fine particles containing a calcium phosphate compound as the major component inside at least a part of the pores of the porous substrate, a coating layer containing a calcium phosphate compound as the major component, i.e., a bone tissue, can be formed and grown on the surface with a high adhesion strength by using the fine particles that have deposited inside the pores as the nuclei. Furthermore, the bioactive composites possesses a characteristic feature as such that, since the fine particles containing a calcium phosphate compound as the major component are deposited inside the pores that are located even in the deep part of the substrate, the bioactivity remains even if processing such as cutting or whittling is applied thereto. Furthermore, the bioactive composites may be implanted in the bodies after forming and growing beforehand the coating layer containing a calcium phosphate compound as the major component on the surface thereof by using the simulated body fluid and the like. Moreover, the addition of functional groups such as a hydroxyl group to the surface by applying a plasma surface treatment to the porous substrate prior to the step (1) enables forming and growing in vivo or in vitro, the coating layer containing a calcium phosphate compound as the major component with a higher adhesion strength.

EXAMPLES

The present invention is explained in further detail by way of Examples below, but the present invention should not be understood as limited thereto.

Example 1

A porous substrate, i.e., a 15 mm length×10 mm width×2 mm thickness porous shaped body comprising ultrahigh molecular weight polyethylene (UHMWPE) (manufactured by NITTO DENKO CORPORATION; having an average pore diameter of 17 μm and a porosity of 26%), was immersed in 2.0SBF whose pH was controlled to 7.0 by adding therein tris(hydroxymethyl) aminomethane under a liquid temperature of 36.5° C., and was subjected to a degassing treatment using a vacuum pump. Subsequently, tris(hydroxymethyl) aminomethane was added to the 2.0SBF having immersed therein the substrate to control the pH to 8.2 at 36.5° C. (at which point it became white clouded in the 2.0SBF), and the resulting product was allowed to stand still for 24 hours. After passage of 24 hours, the substrate was taken out from the 2.0SBF, rinsed with ultrapure water, and air dried. Then, the substrate subjected to the treatment above (Sample A) was immersed in 1.0SBF (pH 7.4) at 36.5° C. for 14 days to study its bioactivity. Table 1 shows the composition of inorganic ions of the plasma, 1.0SBF, and 2.0SBF.

TABLE 1

| | Concentration (mM) | | |
|---|---|---|---|
| Ions | Plasma | 1.0SBF | 2.0SBF |
| $Na^+$ | 142.0 | 142.0 | 284.0 |
| $K^+$ | 5.0 | 5.0 | 10.0 |
| $Mg^{2+}$ | 1.5 | 1.5 | 3.0 |
| $Ca^{2+}$ | 2.5 | 2.5 | 5.0 |
| $Cl^-$ | 103.0 | 147.8 | 295.6 |
| $HCO_3^-$ | 27.0 | 4.2 | 8.4 |
| $HPO_4^{2-}$ | 1.0 | 1.0 | 2.0 |
| $SO_4^{2-}$ | 0.5 | 0.5 | 1.0 |

Figure 2:
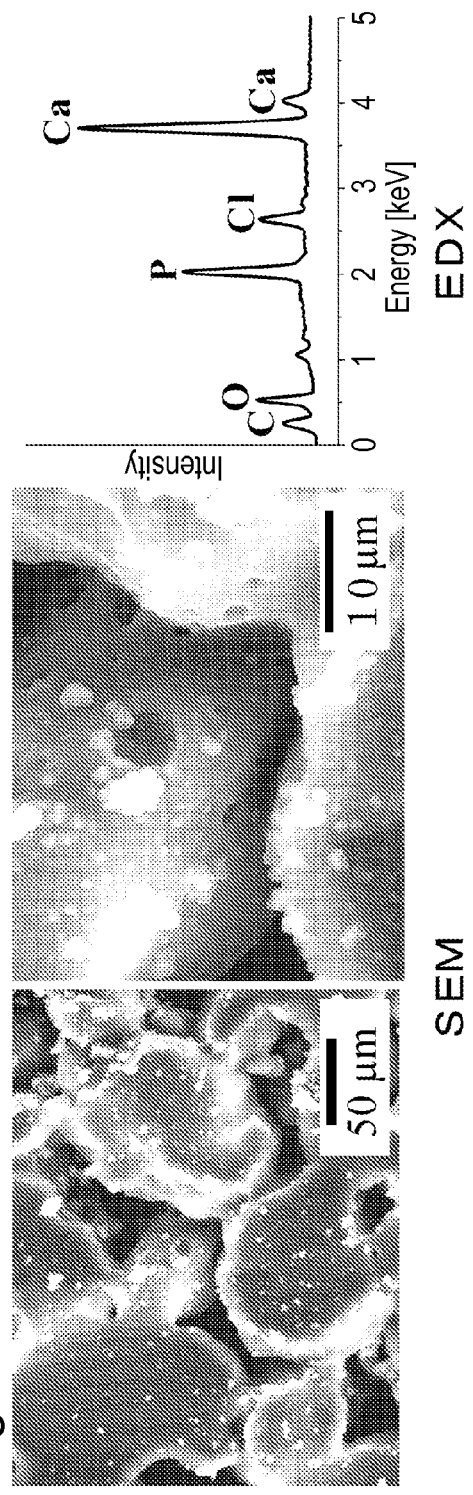
[FIG. 2] It shows the results obtained by SEM and EDX observations of the surface of Sample A, which has been left for 4 days after immersion in 1.0SBF in the same Example 1.
Figure 3:
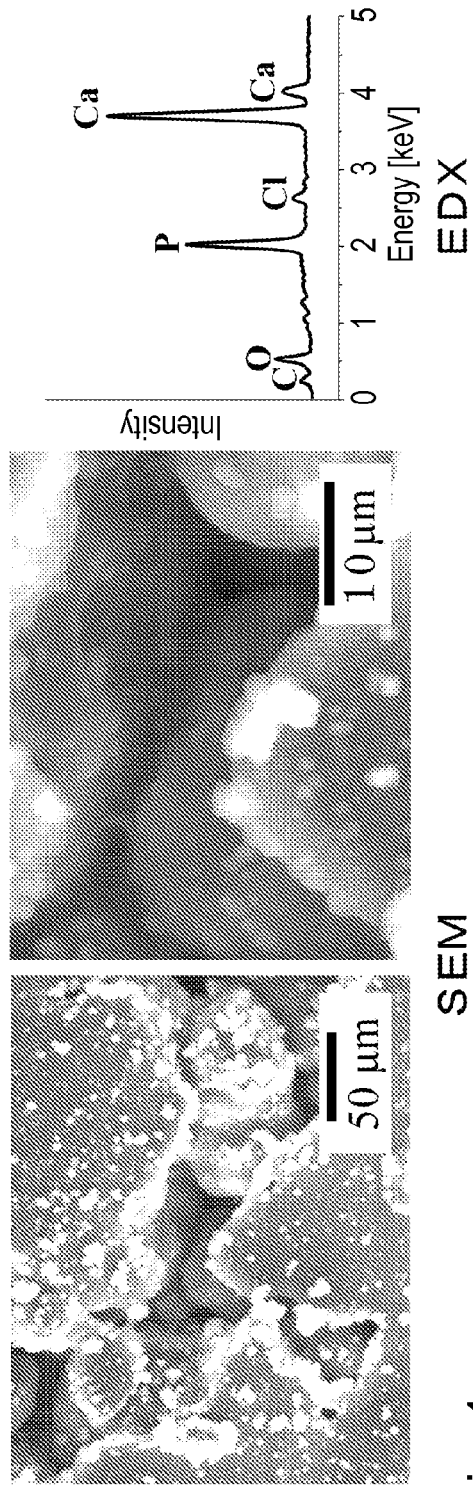
[FIG. 3] It shows the results obtained by SEM and EDX observations of the surface of Sample A, which has been left for 7 days after immersion in 1.0SBF in the same Example 1.
Figure 4:
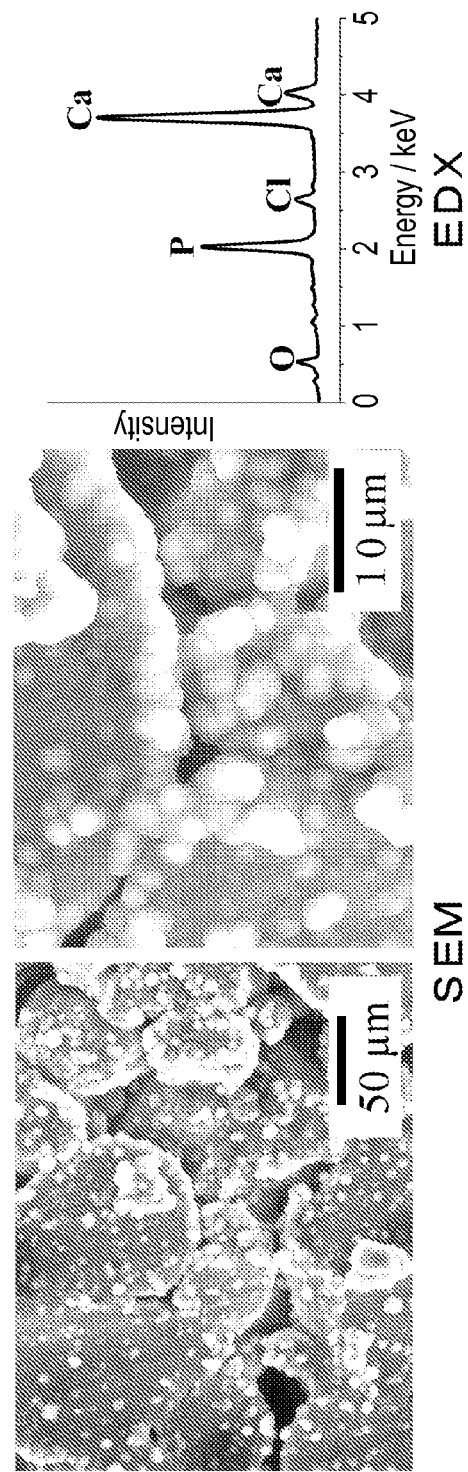
[FIG. 4] It shows the results obtained by SEM and EDX observations of the surface of Sample A, which has been left for 14 days after immersion in 1.0SBF in the same Example 1.
Figure 5:
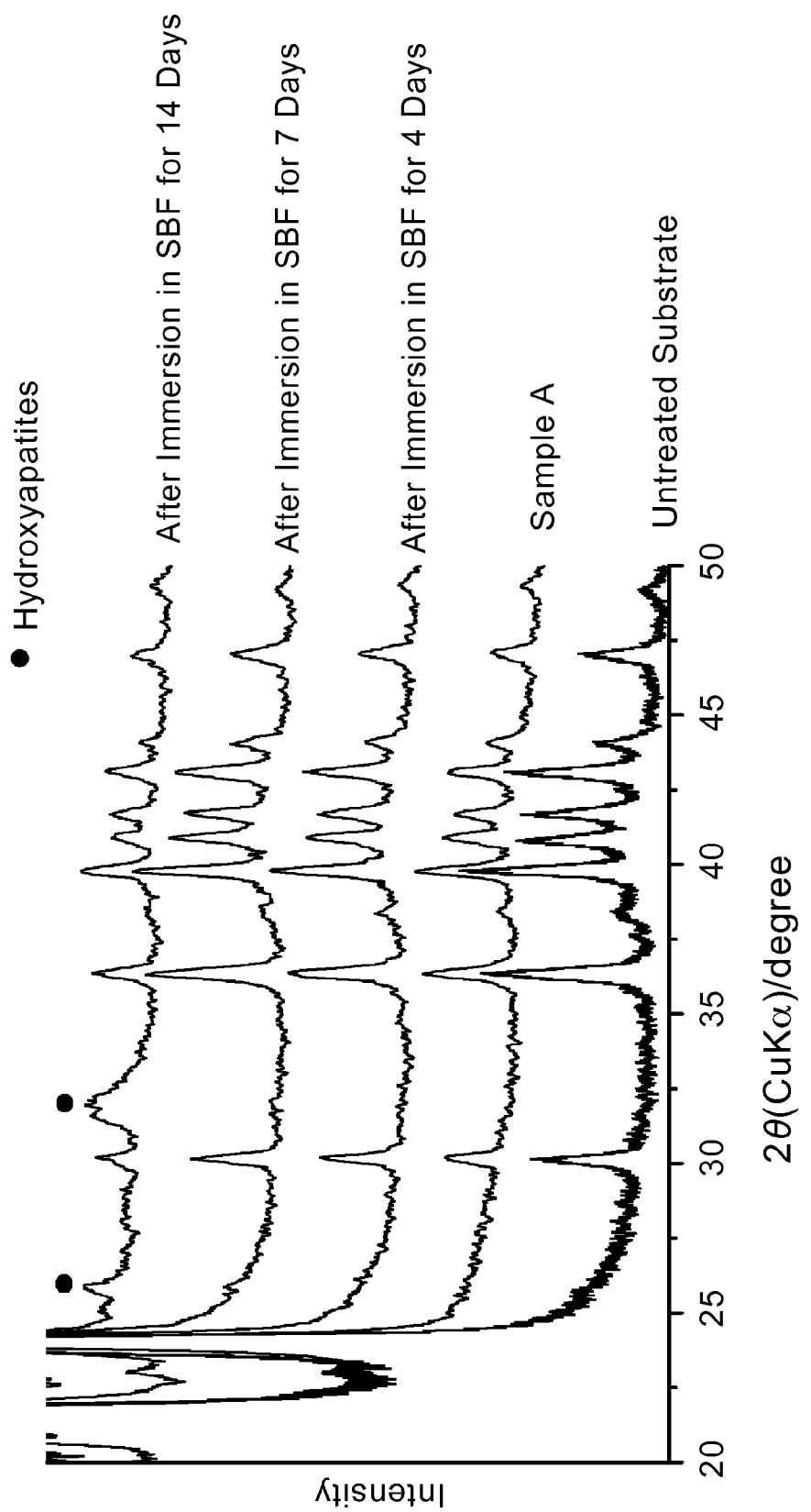
[FIG. 5] It shows the results obtained by TF-XRD observation of the surface of an untreated substrate, Sample A, and Samples A which has been left for 4 days, 7 days, and 14 days after immersion in 1.0SBF in the same Example 1.
Figure 6:
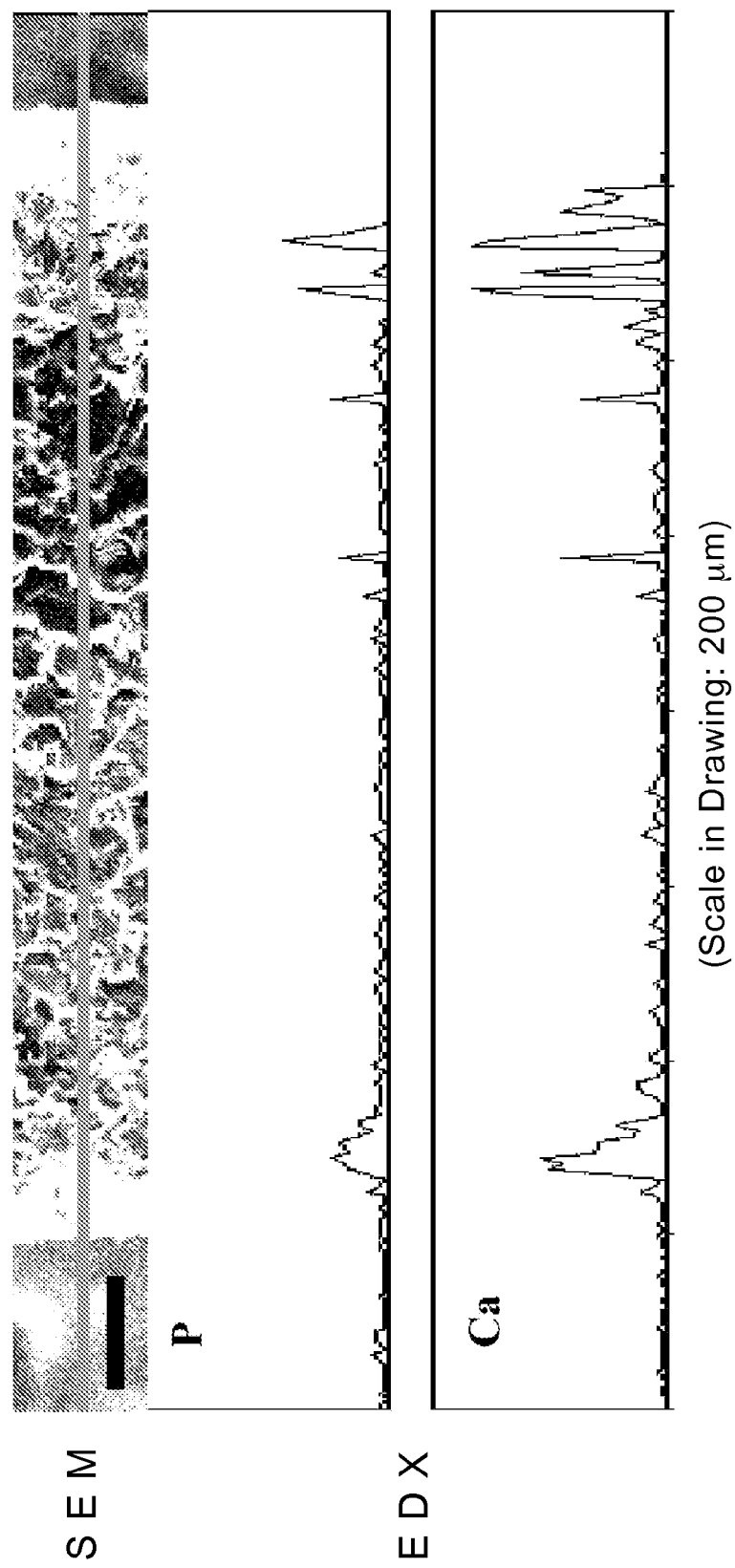
[FIG. 6] It shows the results obtained by SEM and EDX observations of the cross section of sample A, which has been left for 14 days after immersion in 1.0SBF in the same Example 1.

The results obtained by SEM (Scanning Electron Microscope) and EDX (Energy Dispersive X-ray Analyzer) observations of the surface of Sample A with are given in FIG. 1. The results obtained by SEM and EDX observations of the surface of Sample A immersed in 1.0SBF for 4 days, 7 days, and 14 days are given in FIG. 2, FIG. 3, and FIG. 4, respectively. Furthermore, the results obtained by TF-XRD (Thin Film X-ray Diffractometer) observation of the surface of an untreated substrate, Sample A, and the Samples A immersed in 1.0SBF for 4 days, 7 days, and 14 days, are given in FIG. 5. FIG. 6 shows the results obtained by SEM and EDX observations of the cross section of Sample A immersed in 1.0SBF for 14 days.

As is clearly understood from FIG. 1, numerous fine particles of nanometer order containing amorphous calcium phosphate as the major component were found to deposit and adhere to the inside of the fine pores of the substrate of Sample A. Furthermore, as is clarified in FIG. 2 to FIG. 4, a coating layer containing hydroxyapatites as the major component was found to gradually form and grow on the surface of Sample A by immersion in 1.0SBF. Additionally, FIG. 5 reads clearly that a peak indicating the crystalline structure of hydroxyapatites is detected on the surface of Sample A immersed in 1.0SBF for 14 days. Moreover, referring to FIG. 6, it is apparently read in the depth range of about 200 μm to 500 μm from the surface of the substrate on the cross section of Sample A immersed in 1.0SBF for 14 days that the peaks for calcium and phosphorus are detected at positions corresponding to those constituting hydroxyapatites.

From the results above, Sample A comprising the fine particles containing hydroxyapatites as the major component which have deposited inside the fine pores of the substrate, was found to be bioactive composites having bioactivity imparted thereto, in which the fine particles function as nuclei for forming and growing on the surface of the substrate, a coating layer containing hydroxyapatites as the major component.

The adhesion strength of the coating layer containing hydroxyapatites as the major component on Sample A immersed in 1.0SBF for 14 days to the substrate was measured in the following manner. Stainless steel jigs (10×10mm²) were adhered using an epoxy-based adhesive (trade name: Araldite, produced by Huntsman Advanced Materials) to the surface of the coating layer which have been formed on one side of Sample A and to the surface of the other side of the substrate which has been exposed by peeling off the coating layer, and after air-drying for about one week, the jigs were pulled at a crosshead speed of 1 mm/min by using a universal testing machine to thereby obtain the adhesion strength by reading the strength at which the coating layer was separated from the substrate at the contact plane. On measuring 12 samples, an average adhesion strength of 4.2 MPa was obtained with a standard deviation of 0.8 MPa, and the coating layer containing hydroxyapatites as the major component of Sample A was found to be formed and grown on the surface of the substrate with high adhesion strength.

Example 2

Experiments were conducted under the conditions similar to those used in Example 1, except for using, as the solution for depositing fine particles containing hydroxyapatites as the major components inside the fine pores of the substrate, 1.0SBF whose pH was controlled to 7.0 by adding therein tris(hydroxymethyl) aminomethane under a liquid temperature of 36.5° C., and controlling the increase of pH values to 7.2, 7.4, 7.6, 7.8, and 8.0 by adding tris(hydroxymethyl) aminomethane at 60° C. As a result, it has been found that bioactivity can be imparted to the substrate under the above conditions, and that a coating layer containing hydroxyapatites as the major component can be formed and grown on the surface of the substrate.

Example 3

Figure 8:
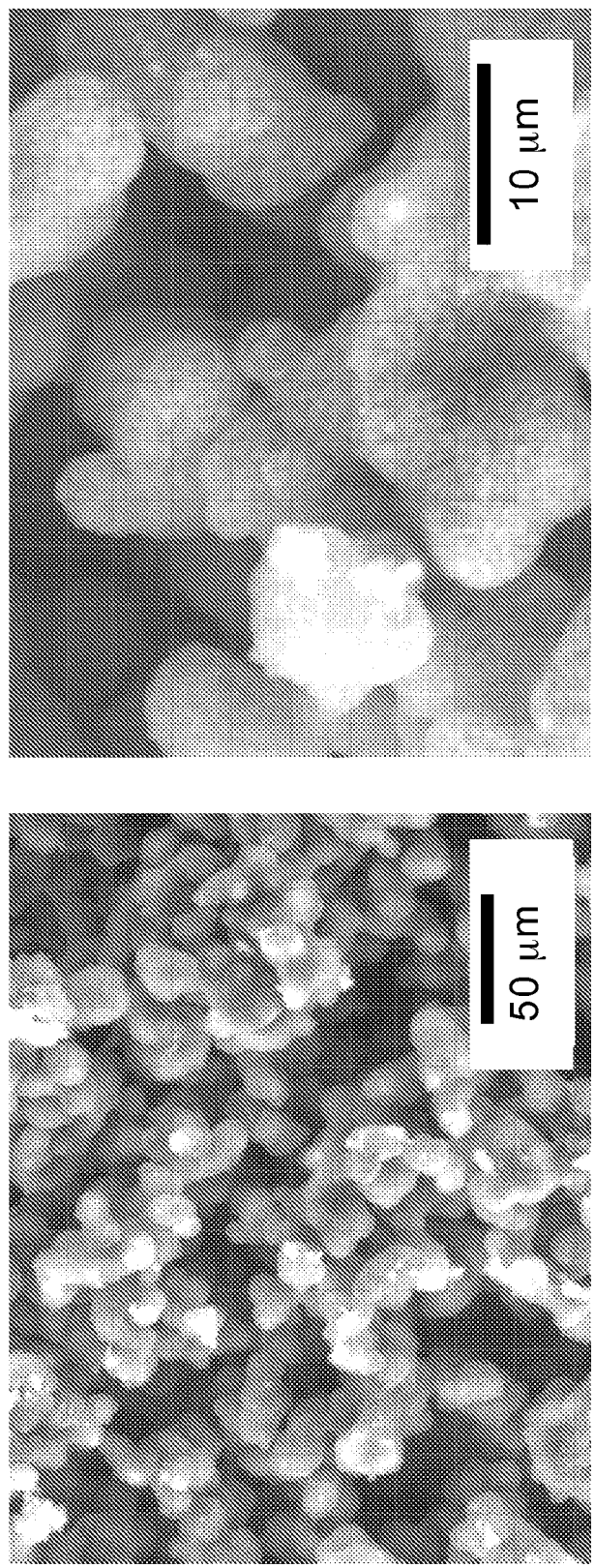
[FIG. 8] It shows the result obtained by SEM observation of the surface of Sample B, which has been left for 14 days after immersion in 1.0SBF in the same Example 3.
Figure 9:
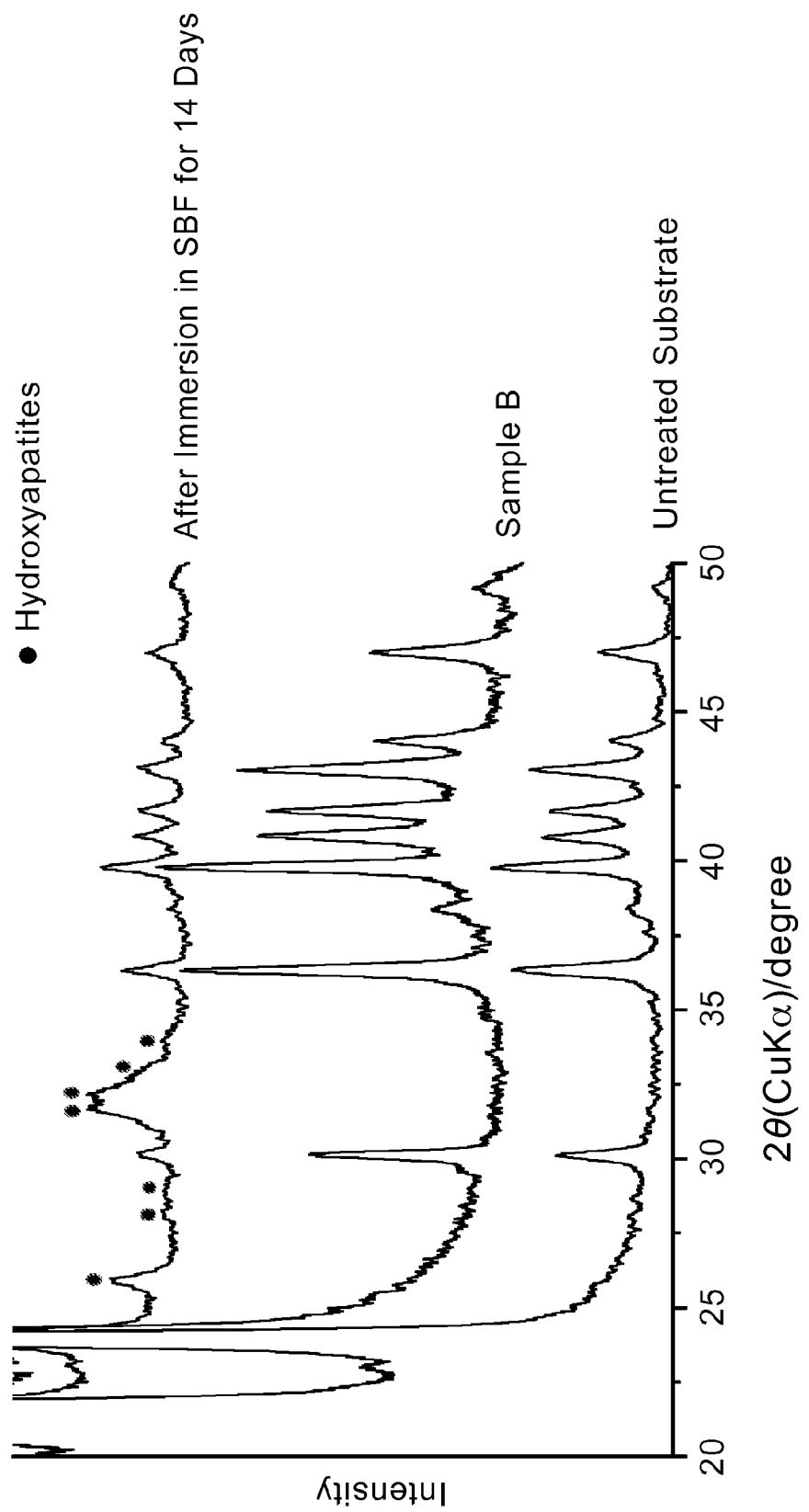
[FIG. 9] It shows the results obtained by TF-XRD observation of the surface of an untreated substrate, Sample B, and Sample B which has been left for 14 days after immersion in 1.0SBF in the same Example 3.

Experiments were conducted under the conditions similar to those used in Example 1, except for using a 15 mm length× 10 mm width×3.2 mm thickness porous shaped body comprising ultrahigh molecular weight polyethylene (UHMWPE) (manufactured by Mitsubishi Plastics, Inc.; having an average pore diameter of 9 μm and a porosity of 52%) as a porous substrate. FIG. 7 shows the results obtained by SEM observation of the surface of the substrate subjected to a treatment for imparting bioactivity (Sample B), and FIG. 8 shows the results obtained by SEM observation of the surface of Sample B immersed in 1.0SBF for 14 days. Furthermore, FIG. 9 shows the results obtained by TF-XRD observation of the surface of an untreated substrate, Sample B, and Sample B immersed in 1.0SBF for 14 days. As FIG. 7 clearly shows, numerous fine particles of nanometer order containing amorphous calcium phosphate as the major component were found to deposit and adhere to the inside of the fine pores of the substrate of Sample B. Furthermore, as is clarified in FIG. 8, a coating layer containing hydroxyapatites as the major component was found to gradually form and grow on the surface of Sample B by immersion in 1.0SBF. Additionally, FIG. 9 reads clearly that a peak indicating the crystalline structure of hydroxyapatites is detected on the surface of Sample B immersed in 1.0SBF for 14 days. It was thereby found from the results above that Sample B is bioactive composites having bioactivity imparted thereto.

Example 4

Experiments were conducted under the conditions similar to those used in Example 1, except for using a 20 mm length× 20 mm width×2 mm thickness porous shaped body comprising alumina (manufactured by Kyushuceramics industries Co., Ltd.; having an average pore diameter of 10 μm and a porosity of 40%) as a porous substrate. As a result, it has been found that bioactivity can be imparted to this substrate, and that a coating layer containing hydroxyapatites as the major component can be formed and grown on the surface of the substrate.

Example 5

Experiments were conducted under the conditions similar to those used in Example 1, except for using a 20 mm length× 20 mm width×2 mm thickness foamed body comprising polylactic acid (manufactured by KASAHARA Industry Co., Ltd.) as a porous substrate. As a result, it has been found that bioactivity can be imparted to this substrate, and that a coating layer containing hydroxyapatites as the major component can be formed and grown on the surface of the substrate.

Example 6

Experiments were conducted under the conditions similar to those used in Example 1, except for using a 10 mm length× 10 mm width (approximate size) felt comprising polylactic acid (manufactured by COREFRONT Corporation) as a porous substrate. As a result, it has been found that bioactivity can be imparted to this substrate, and that a coating layer containing hydroxyapatites as the major component can be formed and grown on the surface of the substrate.

Example 7

Figure 10:
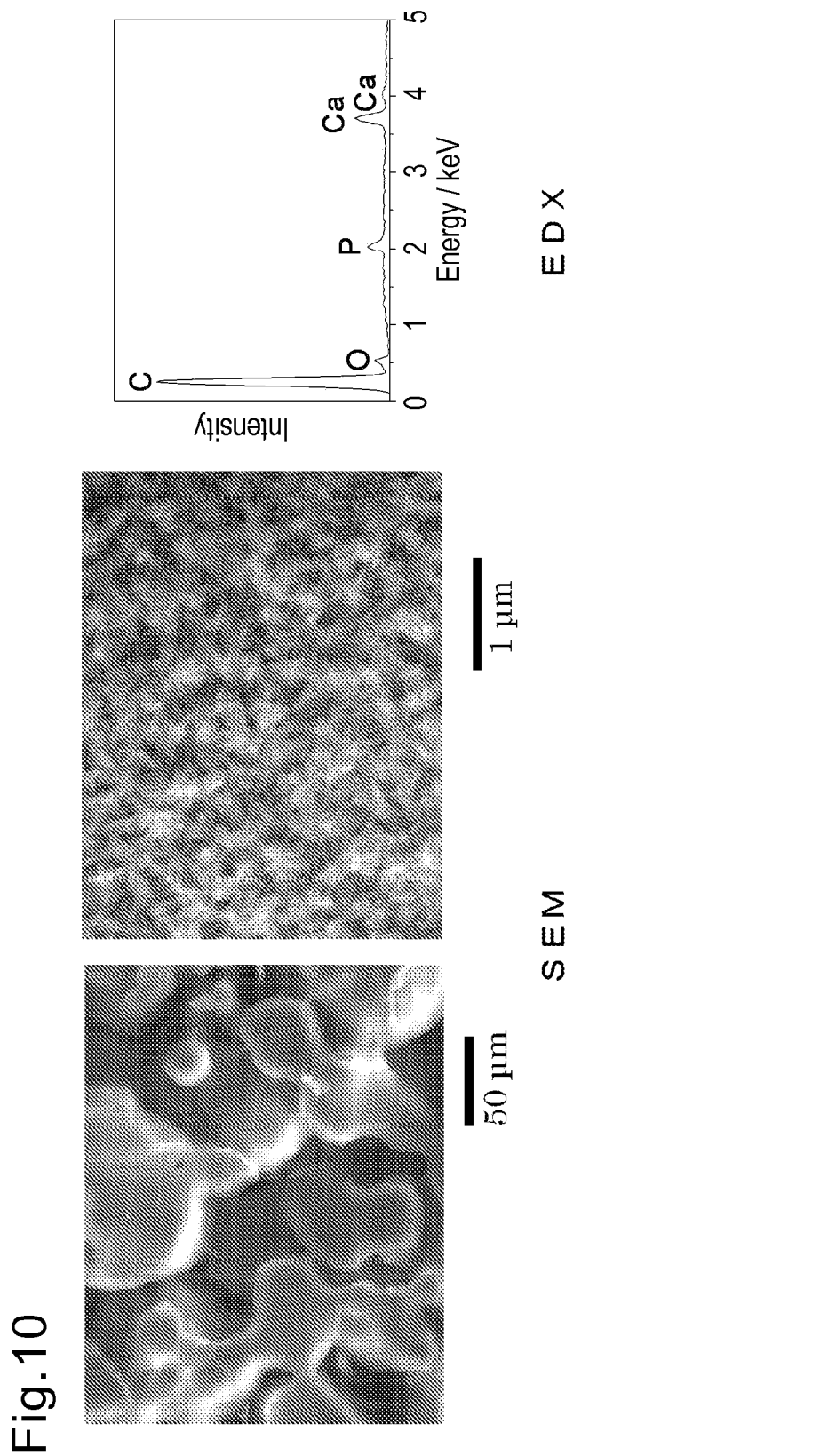
[FIG. 10] It shows the results obtained by SEM and EDX observations of the surface of a substrate subjected to a treatment for imparting bioactivity (Sample C) in Example 7.
Figure 11:
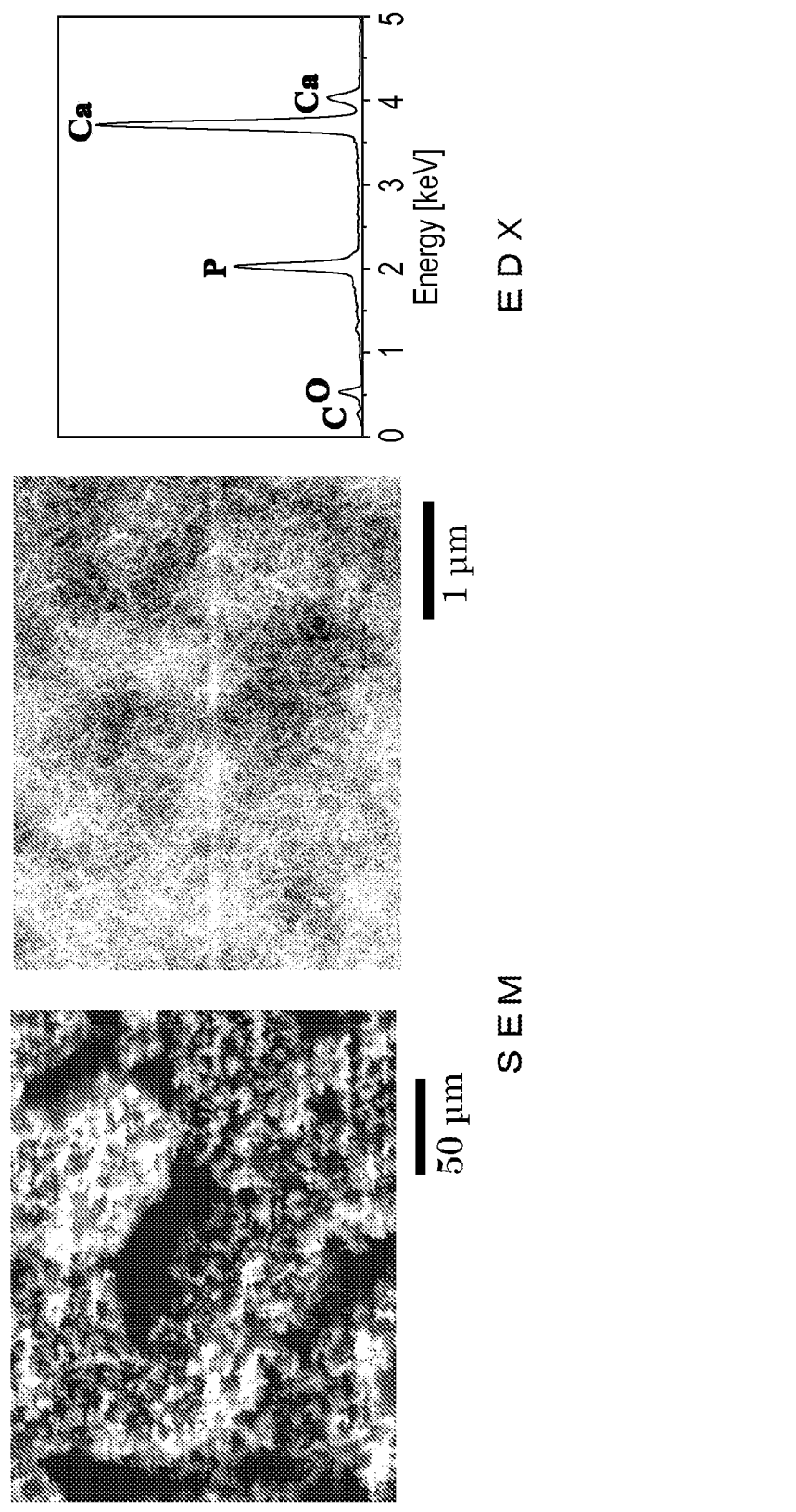
[FIG. 11] It shows the results obtained by SEM and EDX observations of the surface of Sample C, which has been left for 14 days after immersion in 1.0SBF in the same Example 7.

A porous substrate, i.e., a 15 mm length×10 mm width×2 mm thickness porous shaped body comprising ultrahigh molecular weight polyethylene (UHMWPE) (manufactured by NITTO DENKO CORPORATION; having an average pore diameter of 17 μm and a porosity of 26%), was immersed in 1.0SBF whose pH was controlled to 8.0 by adding therein tris(hydroxymethyl) aminomethane under a liquid temperature of 36.5° C., and the temperature was elevated to 60° C., at which temperature the resulting product was allowed to stand still for 24 hours in an incubator set at 60° C. After passage of 24 hours, the substrate was taken out from the 1.0SBF, rinsed with ultrapure water, and air dried. Then, the substrate subjected to the treatment above (Sample C) was immersed in 1.0SBF (pH 7.4) at 36.5° C. for 14 days to study its bioactivity. The results obtained SEM and EDX observations of the surface of Sample C are given in FIG. 10, and the results obtained by SEM and EDX observations of the surface of Sample C immersed in 1.0SBF for 14 days are given in FIG. 11. As FIG. 10 clearly shows, numerous fine particles of nanometer order containing amorphous calcium phosphate as the major component were found to deposit and adhere to the inside of the fine pores of the substrate of Sample C. Furthermore, as is clarified in FIG. 11, a coating layer containing hydroxyapatites as the major component was found to gradually form and grow on the surface of Sample C by immersion in 1.0SBF. It was thereby found from the results above that Sample C is bioactive composites having bioactivity imparted thereto.

Example 8

An oxygen plasma treatment by glow discharge (at a plasma electric power density of 1 W/cm$^2$) was applied for 30 seconds to the surface of a 15 mm length×10 mm width×2 mm thickness porous shaped body comprising ultrahigh molecular weight polyethylene (UHMWPE) (manufactured by NITTO DENKO CORPORATION; having an average pore diameter of 17 μm and a porosity of 26%) to use as a porous substrate. The substrate was immersed in 1.0SBF whose pH was controlled to 8.0 by adding therein tris(hydroxymethyl)aminomethane under a liquid temperature of 36.5° C., and the temperature was elevated to 60° C., at which temperature the resulting product was allowed to stand still for 24 hours in an incubator set at 60° C. After passage of 24 hours, the substrate was taken out from the 1.0SBF, rinsed with ultrapure water, and air dried. Subsequently, the substrate to which bioactivity was imparted by applying the treatment above was immersed in 1.0SBF (pH 7.4) at 36.5° C. for 14 days to form and grow on the surface thereof, a coating layer containing hydroxyapatites as the major component. The adhesion strength of the coating layer containing hydroxyapatites as the major component to the substrate was measured on 8 samples according to the method similar to that described in Example 1, and as a result, an average adhesion strength of 6.9 MPa was obtained with a standard deviation of 1.4 MPa. On the other hand, an average adhesion strength of 10 samples having formed and grown on the surface of the substrate, a coating layer containing hydroxyapatites as the major component under similar conditions as above, except for not applying the oxygen plasma treatment by glow discharge, was 4.6 MPa with a standard deviation of 0.8 MPa. From the results above, it has been found that, by applying a plasma surface treatment to the porous substrate, a coating layer containing hydroxyapatites as the major component can be formed and grown on the surface of the substrate with a higher adhesion strength. It is presumed that functional groups such as a hydroxyl group that have been added to the surface of the substrate by the plasma surface treatment contribute to chemically fixing the coating layer containing hydroxyapatites as the major component to the surface of the substrate to make this effect.

Example 9

Figure 12:
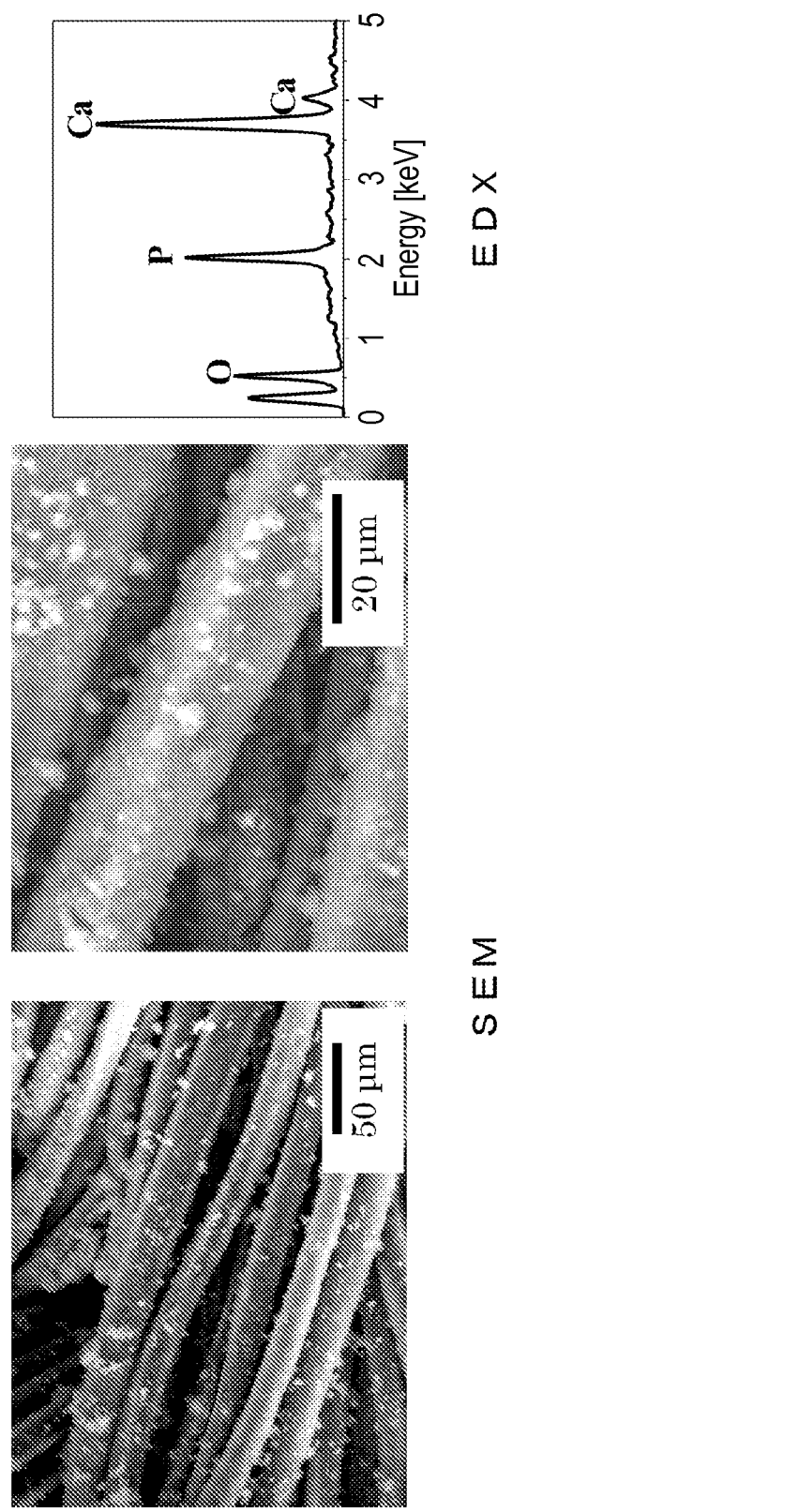
[FIG. 12] It shows the results obtained by SEM and EDX observations of the surface of a substrate subjected to a treatment for imparting bioactivity (Sample D) and which has been left for 14 days after immersion in 1.0SBF in Example 9.

A polyester woven cloth (white colored, purchased from Nomura-tailor. Corporation) was used as a porous substrate, which was immersed in 2.0SBF whose pH was controlled to 7.0 by adding therein tris(hydroxymethyl)aminomethane under a liquid temperature of 36.5° C. Subsequently, tris (hydroxymethyl)aminomethane was added to the 2.0SBF having immersed therein the substrate to control the pH to 8.2 at 36.5° C., and the resulting product was allowed to stand still for 24 hours. After passage of 24 hours, the substrate was taken out from the 2.0SBF, rinsed with ultrapure water, and air dried. Then, the substrate to which bioactivity was imparted by applying the treatment above (Sample D) was immersed in 1.0SBF (pH 7.4) at 36.5° C. for 14 days. The results obtained by SEM and EDX observations of the surface of Sample D immersed in 1.0SBF for 14 days are given in FIG. 12. As is shown clearly in FIG. 12, a coating layer containing hydroxyapatites as the major component was found to gradually form and grow on the surface of Sample D by immersion in 1.0SBF.

Example 10

Figure 13:
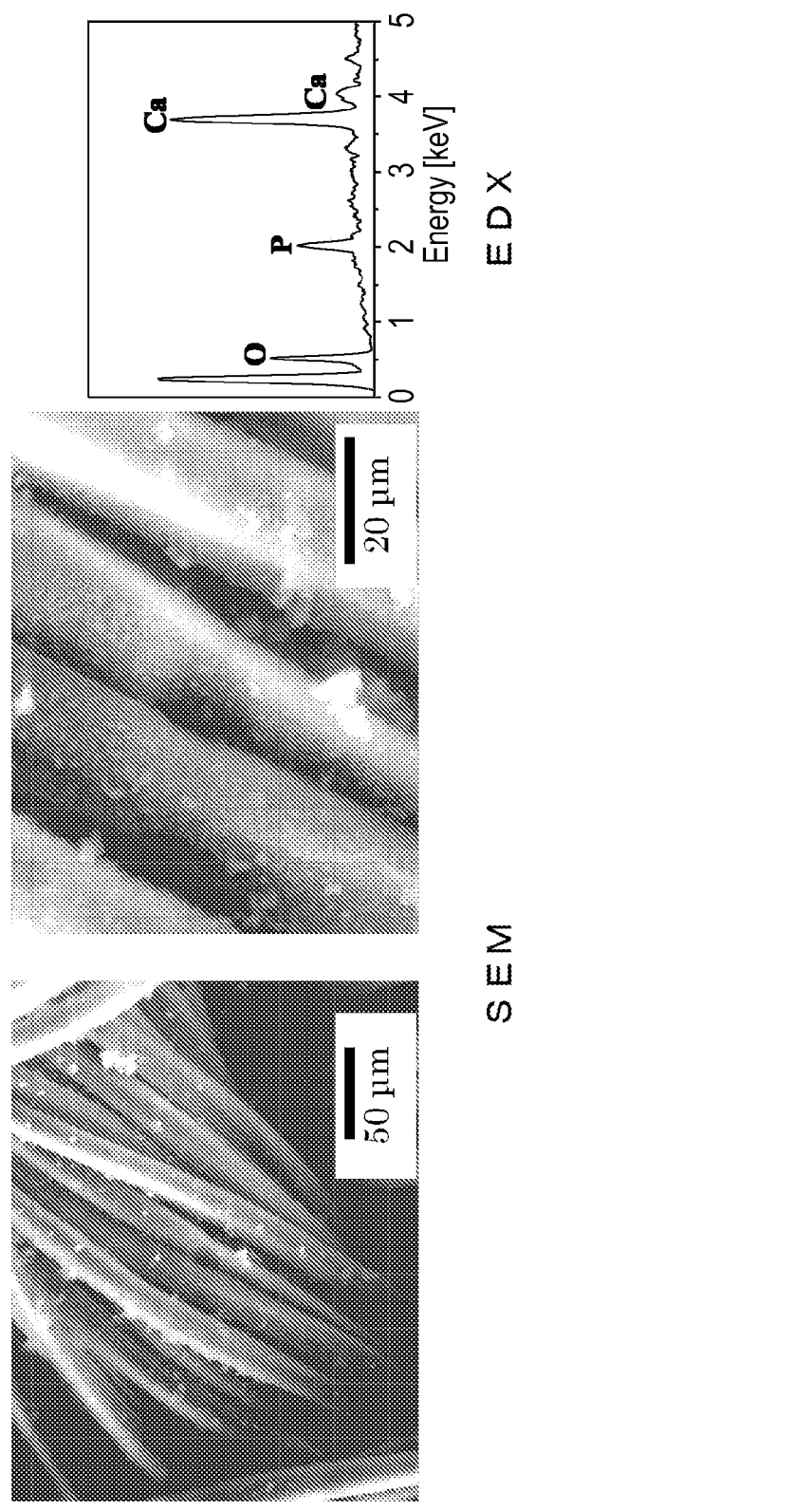
[FIG. 13] It shows the results obtained by SEM and EDX observations of the surface of a substrate subjected to a treatment for imparting bioactivity (Sample E) and which has been left for 14 days after immersion in 1.0SBF in Example 10.

A polyester woven cloth (white colored, purchased from Nomura-tailor. Corporation) was used as a porous substrate, which was immersed in 1.0SBF whose pH was controlled to 8.0 by adding therein tris(hydroxymethyl)aminomethane under a liquid temperature of 36.5° C., and the temperature was elevated to 60° C., at which temperature the resulting product was allowed to stand still for 24 hours in an incubator set at 60° C. After passage of 24 hours, the substrate was taken out from the 1.0SBF, rinsed with ultrapure water, and air dried. Then, the substrate to which bioactivity was imparted by applying the treatment above (Sample E) was immersed in 1.0SBF (pH 7.4) at 36.5° C. for 14 days. The results obtained by SEM and EDX observations of the surface of Sample E immersed in 1.0SBF for 14 days are given in FIG. 13. As is shown clearly in FIG. 13, a coating layer containing hydroxyapatites as the major component was found to gradually form and grow on the surface of Sample E by immersion in 1.0SBF.

Example 11

Experiments were conducted under the conditions similar to those used in Example 10, except for using, as a porous substrate, a polyester woven cloth (white colored, purchased from Nomura-tailor. Corporation) having subjected to an oxygen plasma treatment by glow discharge (at a plasma electric power density of 1 W/cm$^2$) for 30 seconds. As a result, it has been found that bioactivity can be imparted to this substrate, and that a coating layer containing hydroxyapatites as the major component can be formed and grown on the surface of the substrate with a higher adhesion strength.

Example 12

Figure 14:
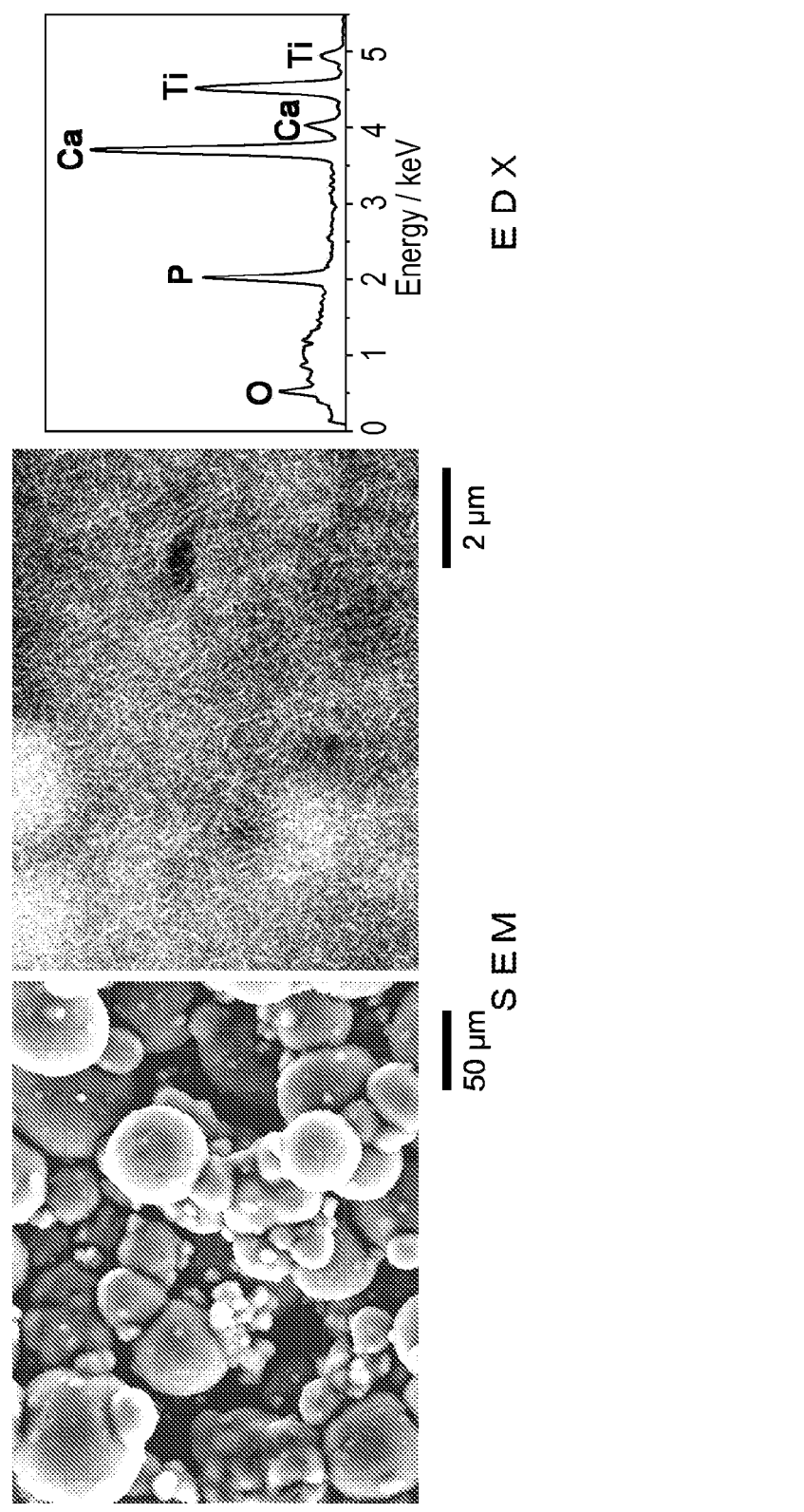
[FIG. 14] It shows the results obtained by SEM and EDX observations of the surface of a substrate subjected to a treatment for imparting bioactivity (Sample F) and which has been left for 14 days after immersion in 1.0SBF in Example 12.

A 10 mm length×10 mm width×1 mm thickness porous titanium plate (manufactured by Sumitomo Titanium Corporation; having an average pore diameter of 25 μm and a porosity of 40%) was cleaned with ethanol and distilled water, and was air dried to use as a porous substrate. The substrate was immersed in 2.0SBF whose pH was controlled to 7.0 by adding therein tris(hydroxymethyl)aminomethane under a liquid temperature of 36.5° C., and was subjected to a degassing treatment using a vacuum pump. Subsequently, tris(hydroxymethyl)aminomethane was added to the 2.0SBF having immersed therein the substrate to control the pH to 8.2 at 36.5° C., and the resulting product was allowed to stand still for 24 hours. After passage of 24 hours, the substrate was taken out from the 2.0SBF, rinsed with ultrapure water, and air dried. Then, the substrate to which bioactivity was imparted by applying the treatment above (Sample F) was immersed in 1.0SBF (pH 7.4) at 36.5° C. for 14 days. The results obtained by SEM and EDX observations of the surface of Sample F immersed in 1.0SBF for 14 days are given in FIG. 14. As FIG. 14 clearly shows, a coating layer containing hydroxyapatites as the major component was found to gradually form and grow on the surface of Sample F by immersion in 1.0SBF. The adhesion strength of the coating layer containing hydroxyapatites as the major component to the substrate was measured on 9 samples according to the method similar to that described in Example 1, and as a result, an average adhesion strength of 7.0 MPa was obtained with a standard deviation of 2.8 MPa.

Example 13

Figure 15:
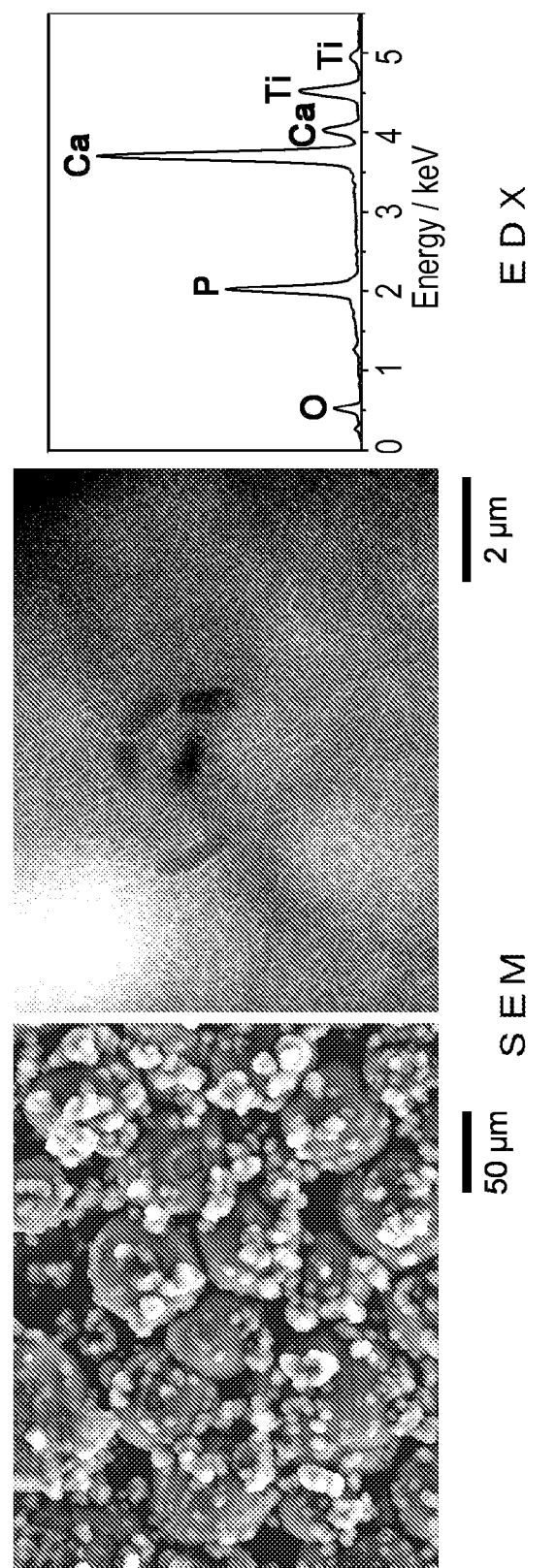
[FIG. 15] It shows the results obtained by SEM and EDX observations of the surface of a substrate subjected to a treatment for imparting bioactivity (Sample G) and which has been left for 14 days after immersion in 1.0SBF in Example 13.

A 10 mm length×10 mm width×1 mm thickness porous titanium plate (manufactured by Sumitomo Titanium Corporation; having an average pore diameter of 25 μm and a porosity of 40%) was cleaned with ethanol and distilled water, and was air dried to use as a porous substrate. The substrate was immersed in 1.0SBF whose pH was controlled to 8.0 by adding therein tris(hydroxymethyl)aminomethane under a liquid temperature of 36.5° C., and was subjected to a degassing treatment using a vacuum pump. Subsequently, the temperature was elevated to 60° C., at which temperature the resulting product was allowed to stand still for 24 hours in an incubator set at 60° C. After passage of 24 hours, the substrate was taken out from the 1.0SBF, rinsed with ultrapure water, and air dried. Then, the substrate to which bioactivity was imparted by applying the treatment above (Sample G) was immersed in 1.0SBF (pH 7.4) at 36.5° C. for 14 days. The results obtained by SEM and EDX observations of the surface of Sample G immersed in 1.0SBF for 14 days are given in FIG. 15. As is shown clearly in FIG. 15, a coating layer containing hydroxyapatites as the major component was found to gradually form and grow on the surface of Sample G by immersion in 1.0SBF.

Example 14

Figure 16:
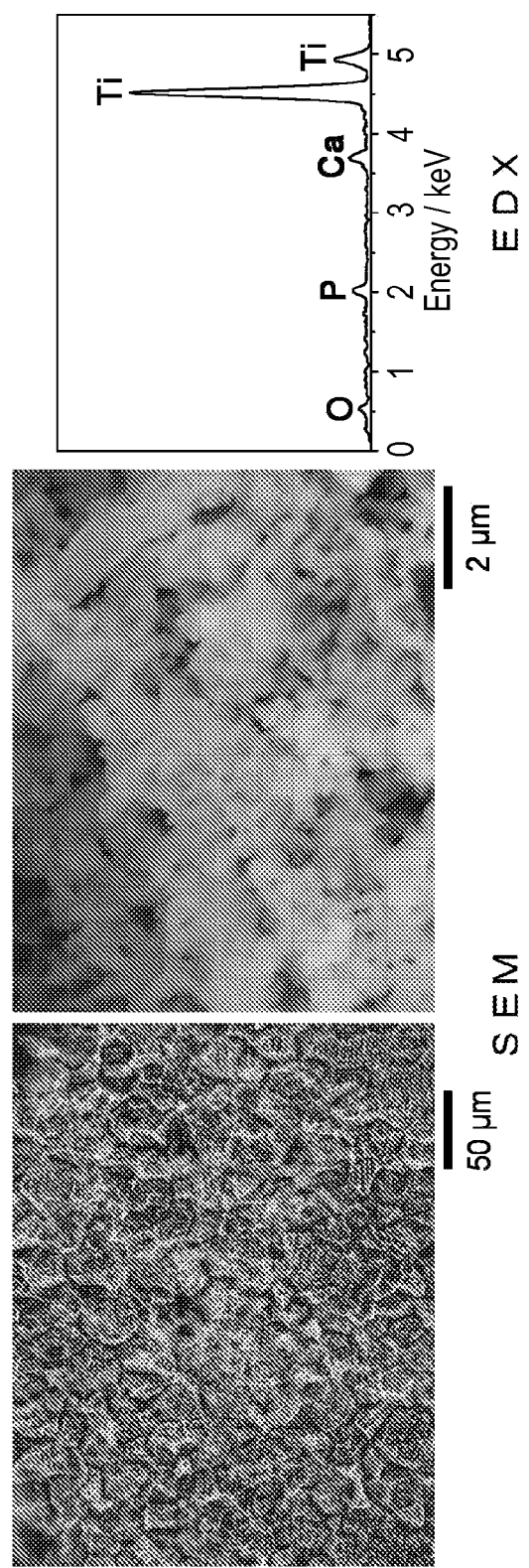
[FIG. 16] It shows the results obtained by SEM and EDX observations of the surface of a substrate subjected to a treatment for imparting bioactivity (Sample H) in Example 14.
Figure 17:
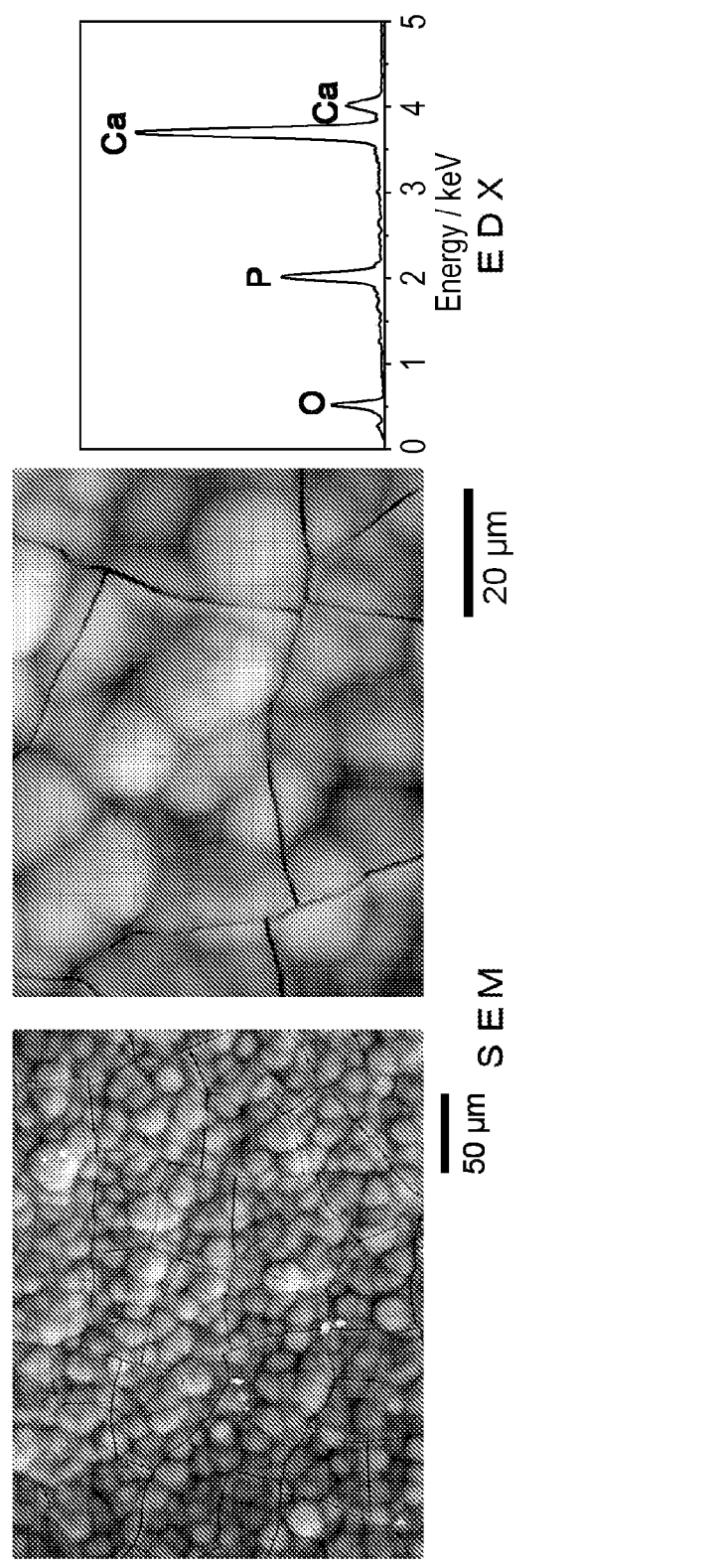
[FIG. 17] It shows the results obtained by SEM and EDX observations of the surface of Sample H, which has been left for 14 days after immersion in 1.0SBF in the same Example 14.

A 10 mm length×10 mm width×1 mm thickness titanium flat plate (manufactured by KOBE STEEL, LTD.) was immersed in 48% sulfuric acid for 60 minutes in an incubator set at 90° C., followed by ultrasonic cleaning in distilled water and air drying to use as a porous substrate. The substrate was immersed in 1.0SBF whose pH was controlled to 8.0 by adding therein tris(hydroxymethyl)aminomethane under a liquid temperature of 36.5° C., and was subjected to a pressurizing treatment (392 MPa) for 1 hour by using a cold isostatic pressing apparatus. Subsequently, the temperature was elevated to 60° C., at which temperature the resulting product was allowed to stand still for 24 hours in an incubator set at 60° C. After passage of 24 hours, the substrate was taken out from the 1.0SBF, rinsed lightly with distilled water, and air dried. Then, the substrate subjected to the treatment above (Sample H) was immersed in 1.0SBF (pH 7.4) at 36.5° C. for 14 days to study its bioactivity. The results obtained by SEM and EDX observations of the surface of Sample H are given in FIG. 16, and the results obtained by SEM and EDX observations of the surface of Sample H immersed in 1.0SBF for 14 days are given in FIG. 17. As is shown clearly in FIG. 16, numerous fine particles of nanometer order containing amorphous calcium phosphate as the major component were found to deposit and adhere to the inside of the fine pores about 1 μm in diameter of the substrate of Sample H. Furthermore, as is clarified in FIG. 17, a coating layer containing hydroxyapatites as the major component was found to gradually form and grow on the surface of Sample H by immersion in 1.0SBF. It was thereby found from the results above that Sample H is bioactive composites having bioactivity imparted thereto. The adhesion strength of the coating layer containing hydroxyapatites as the major component to the substrate was measured on 7 samples according to the method similar to that described in Example 1, and as a result, an average adhesion strength of 8.4 MPa was obtained with a standard deviation of 1.2 MPa. The reason for such a high adhesion strength of the coating layer containing hydroxyapatites as the major component to the substrate was considered attributed to the randomly formed fine pores of the substrate of Sample H with respect to the direction, by which an interlocking effect was effectively functioned. On the other hand, in the case of a porous shaped body, which was produced by immersing a 10 mm length×10 mm width×1 mm thickness titanium flat plate (manufactured by KOBE STEEL, LTD.) in 48% sulfuric acid for 60 minutes in an incubator set at 90° C., followed by ultrasonic cleaning in distilled water and air drying, and which was immersed immediately in 1.0SBF (pH 7.4) at 36.5° C. for 14 days, no coating layer containing hydroxyapatites as the major component was found to either form or grow on the surface thereof.

Example 15

Figure 18:
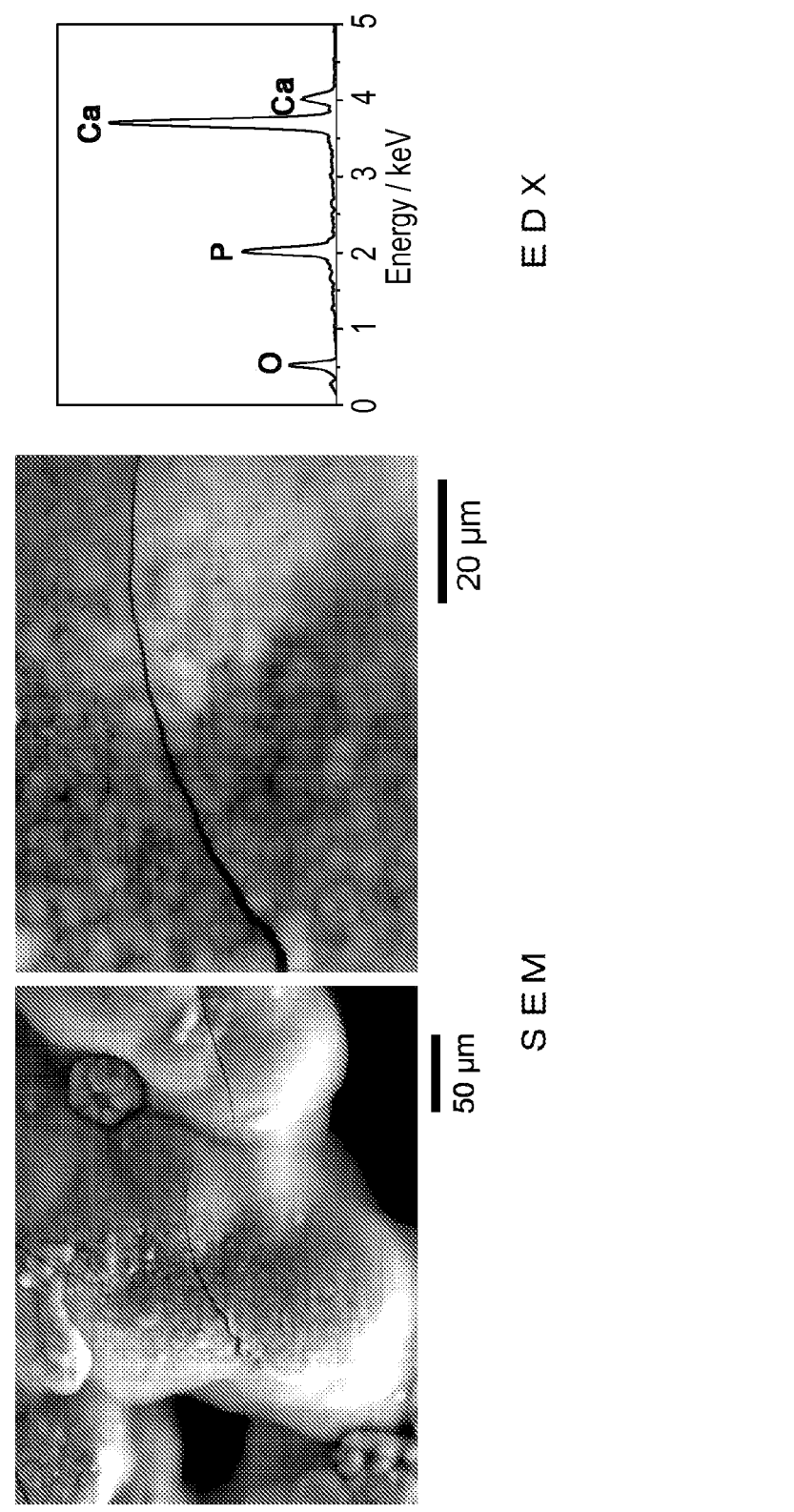
[FIG. 18] It shows the results obtained by SEM and EDX observations of the surface of a substrate subjected to a treatment for imparting bioactivity (Sample I) and which has been left for 14 days after immersion in 1.0SBF in Example 15.

A porous substrate, i.e., a 15 mm length×10 mm width×2 mm thickness porous shaped body comprising ultrahigh molecular weight polyethylene (UHMWPE) (manufactured by NITTO DENKO CORPORATION; having an average pore diameter of 17 μm and a porosity of 26%), was immersed in 1.0SBF whose pH was controlled to 8.0 by adding therein tris(hydroxymethyl) aminomethane under a liquid temperature of 36.5° C., and was subjected to a pressurizing treatment (392 MPa) for 1 hour by using a cold isostatic pressing apparatus. The substrate was placed in a 500 ml beaker, and 1.0SBF at 36.5° C., whose pH was controlled to 8.0 by adding therein tris(hydroxymethyl)aminomethane, was poured therein to make a volume of 150 ml to have the substrate immersed. The beaker was then covered with a wrap, and after penetrating holes in the wrap for vapor escape, was heated using a microwave oven (at a high frequency power output of 500 W and at an oscillatory frequency of 2450 MHz) for 120 seconds (at which point it became white clouded in the 1.0SBF). The substrate was taken out from the beaker, rinsed lightly with distilled water, and air dried. Then, the substrate to which bioactivity was imparted by applying the treatment above (Sample I) was immersed in 1.0SBF (pH 7.4) at 36.5° C. for 14 days. The results obtained by SEM and EDX observations of the surface of Sample I immersed in 1.0SBF for 14 days are given in FIG. 18. As is read clearly from FIG. 18, a coating layer containing hydroxyapatites as the major component was found to gradually form and grow on the surface of Sample I by immersion in 1.0SBF.

Example 16

Figure 19:
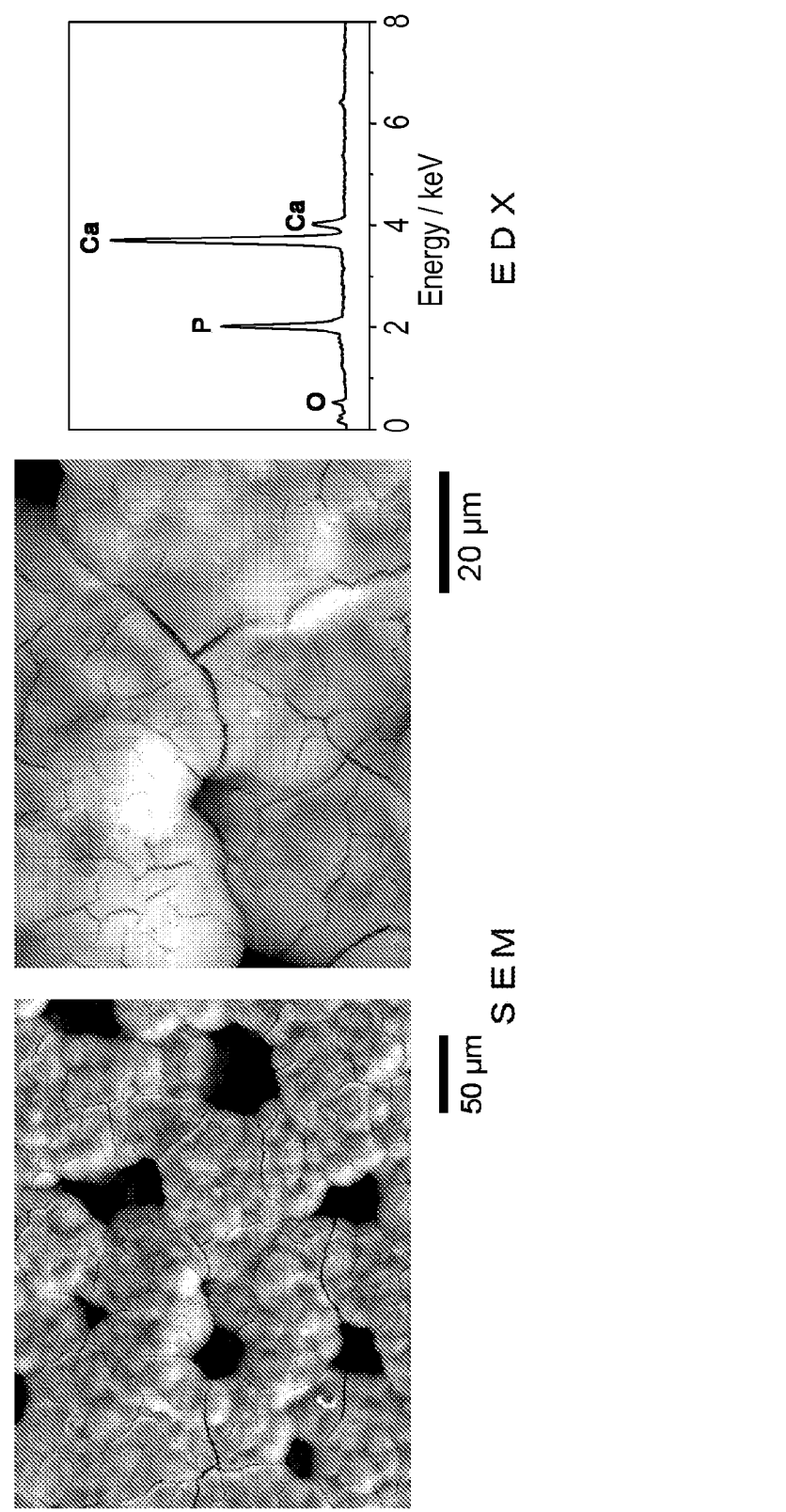
[FIG. 19] It shows the results obtained by SEM and EDX observations of the surface of a substrate subjected to a treatment for imparting bioactivity (Sample J) and which has been left for 14 days after immersion in 1.0SBF in Example 16.

An 8 mm length×8 mm width×1 mm thickness porous stainless steel plate (manufactured by TAISEI KOGYO CO., LTD.; having an average pore diameter of 10 μm and a porosity of 62%) was subjected to ultrasonic cleaning in acetone, and was air dried to use as a porous substrate. The substrate was immersed in 2.0SBF whose pH was controlled to 7.0 by adding therein tris(hydroxymethyl) aminomethane under a liquid temperature of 36.5° C., and was subjected to a degassing treatment using a vacuum pump. Subsequently, tris(hydroxymethyl) aminomethane was added to the 2.0SBF having immersed therein the substrate to control the pH to 8.2 at 36.5° C., and the resulting product was allowed to stand still for 24 hours. After passage of 24 hours, the substrate was taken out from the 2.0SBF, rinsed lightly with distilled water, and air dried. Then, the substrate to which bioactivity was imparted by applying the treatment above (Sample J) was immersed in 1.0SBF (pH 7.4) at 36.5° C. for 14 days. The results obtained by SEM and EDX observations of the surface of Sample J immersed in 1.0SBF for 14 days are given in FIG. 19. As FIG. 19 clearly shows, a coating layer containing hydroxyapatites as the major component was found to gradually form and grow on the surface of Sample J by immersion in 1.0SBF.

Example 17

Figure 20:
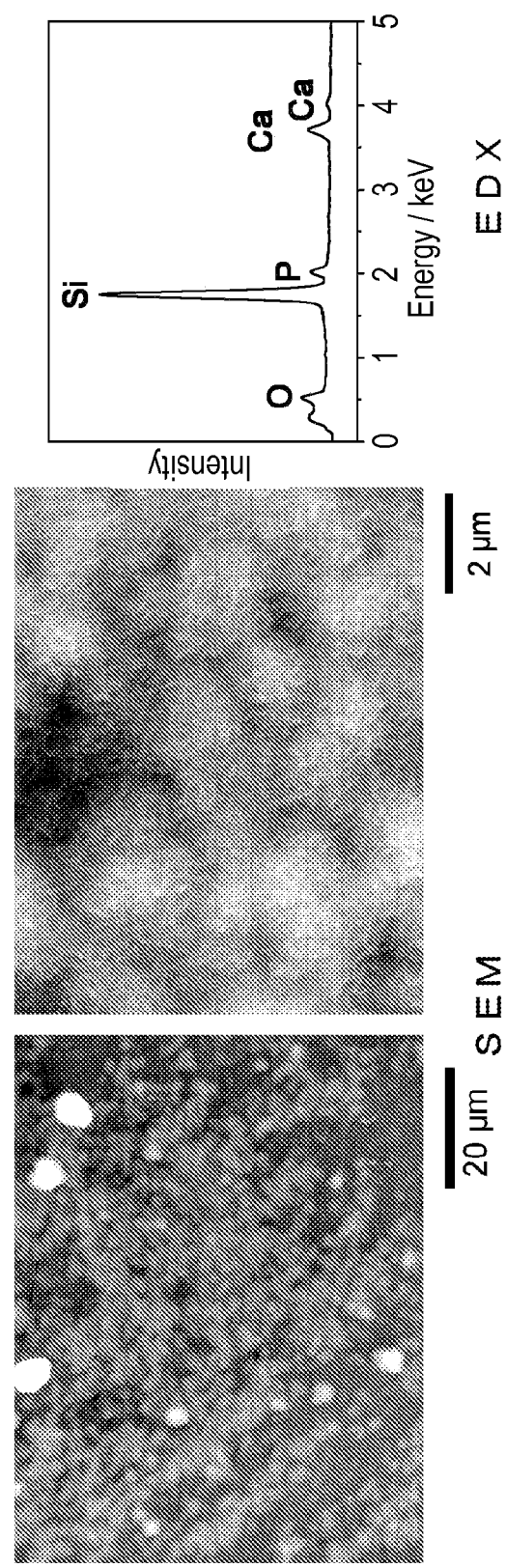
[FIG. 20] It shows the results obtained by SEM and EDX observations of the surface of a substrate subjected to a treatment for imparting bioactivity (Sample K) and which has been left for 7 days after immersion in 1.0SBF in Example 17.

Spherical silica gel particles having a particle distribution in the range of 1.7 mm to 4.0 mm (manufactured by Fuji Silysia Chemical Ltd.; having an average pore diameter of 47 nm and fine pore volume of 1.0 $dm^3 \cdot g^{-1}$) were used as a porous substrate, and were immersed in 1.0SBF whose pH was controlled to 8.0 by adding therein tris(hydroxymethyl) aminomethane under a liquid temperature of 36.5° C. Then, a pressurizing treatment (392 MPa) for 1 hour by using a cold isostatic pressing apparatus was applied thereto. Subsequently, the temperature was elevated to 60° C., at which temperature the resulting product was allowed to stand still for 24 hours in an incubator set at 60° C. After passage of 24 hours, the substrate was taken out from the 1.0SBF, rinsed lightly with distilled water, and air dried. Then, the substrate to which bioactivity was imparted by applying the treatment above (Sample K) was immersed in 1.0SBF (pH 7.4) at 36.5° C. for 7 days. The results obtained by SEM and EDX observations of the surface of Sample K immersed in 1.0SBF for 7 days are given in FIG. 20. As is shown clearly in FIG. 20, a coating layer containing hydroxyapatites as the major component was found to gradually form and grow on the surface of Sample K by immersion in 1.0SBF.

Example 18

Figure 21:
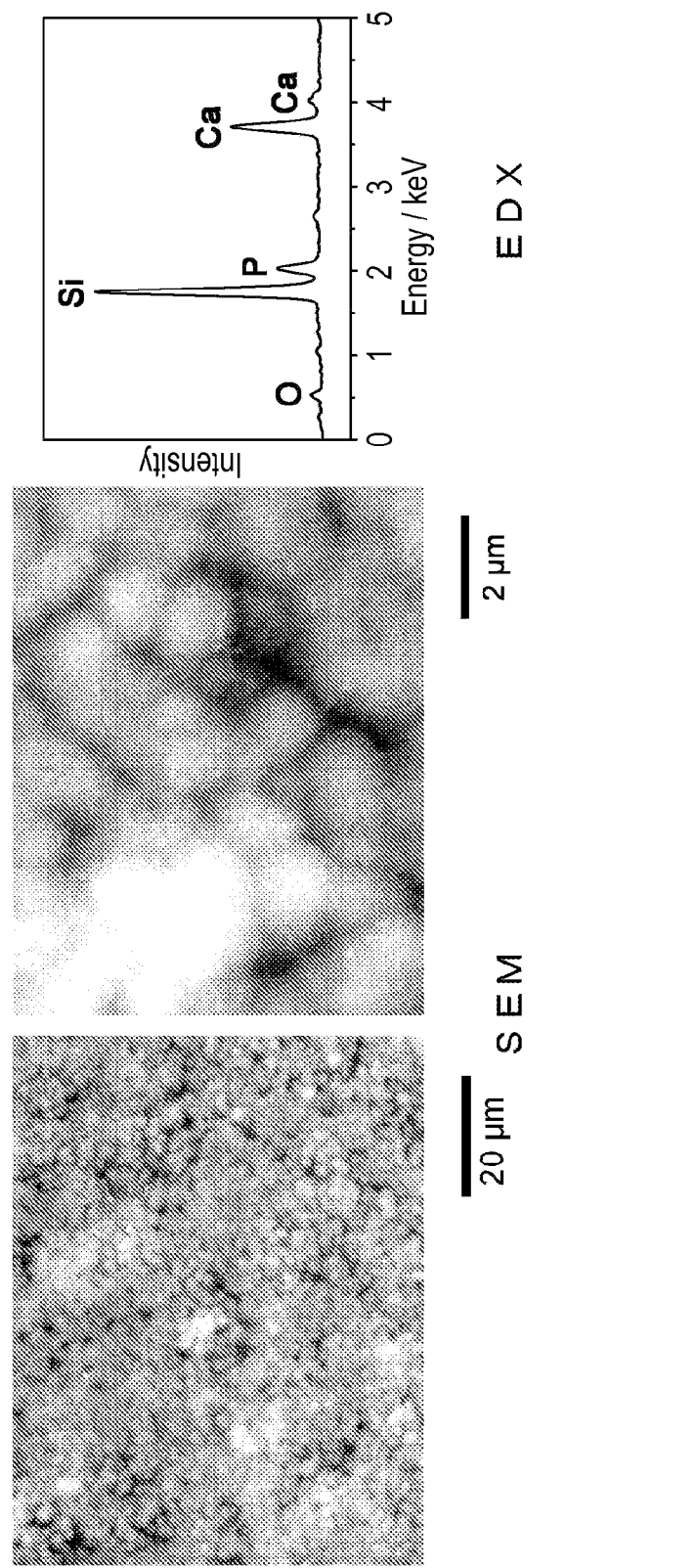
[FIG. 21] It shows the results obtained by SEM and EDX observations of the surface of a substrate subjected to a treatment for imparting bioactivity (Sample L) and which has been left for 7 days after immersion in 1.0SBF in Example 18.

Spherical silica gel particles having a particle distribution in the range of 1.7 mm to 4.0 mm (manufactured by Fuji Silysia Chemical Ltd.; having an average pore diameter of 47 nm and fine pore volume of 1.0 $dm^3 \cdot g^{-1}$) were used as a porous substrate, and were immersed in 1.0SBF whose pH was adjusted to 8.0 by adding therein tris(hydroxymethyl) aminomethane under a liquid temperature of 36.5° C. Then, a pressurizing treatment (392 MPa) for 1 hour by using a cold isostatic pressing apparatus was applied thereto. The substrate was placed in a 500 ml beaker, and 1.0SBF at 36.5° C., whose pH was controlled to 8.0 by adding therein tris(hydroxymethyl)aminomethane, was poured therein to have the substrate immersed. The beaker was then covered with a wrap, and after penetrating holes in the wrap for vapor escape, was heated using a microwave oven (at a high frequency power output of 500 W and at an oscillatory frequency of 2450 MHz) for 120 seconds (at which point it became white clouded in the 1.0SBF). The substrate was taken out from the beaker, rinsed lightly with distilled water, and air dried. Then, the substrate to which bioactivity was imparted by applying the treatment above (Sample L) was immersed in 1.0SBF (pH 7.4) at 36.5° C. for 7 days. The results obtained by SEM and EDX observations of the surface of Sample L immersed in 1.0SBF for 7 days are given in FIG. 21. As is read clearly from FIG. 21, a coating layer containing hydroxyapatites as the major component was found to gradually form and grow on the surface of Sample L by immersion in 1.0SBF.

Example 19

Experiments were conducted under the conditions similar to those used in Example 18, except for using, as the solution for depositing fine particles containing hydroxyapatites as the major component inside the fine pores of the substrate, 1.0SBF whose pH was controlled to 7.85 by adding therein tris(hydroxymethyl) aminomethane under a liquid temperature of 36.5° C. As a result, it has been found that bioactivity can be imparted to the substrate under the above conditions, and that a coating layer containing hydroxyapatites as the major component can be formed and grown on the surface of the substrate.

Example 20

Figure 22:
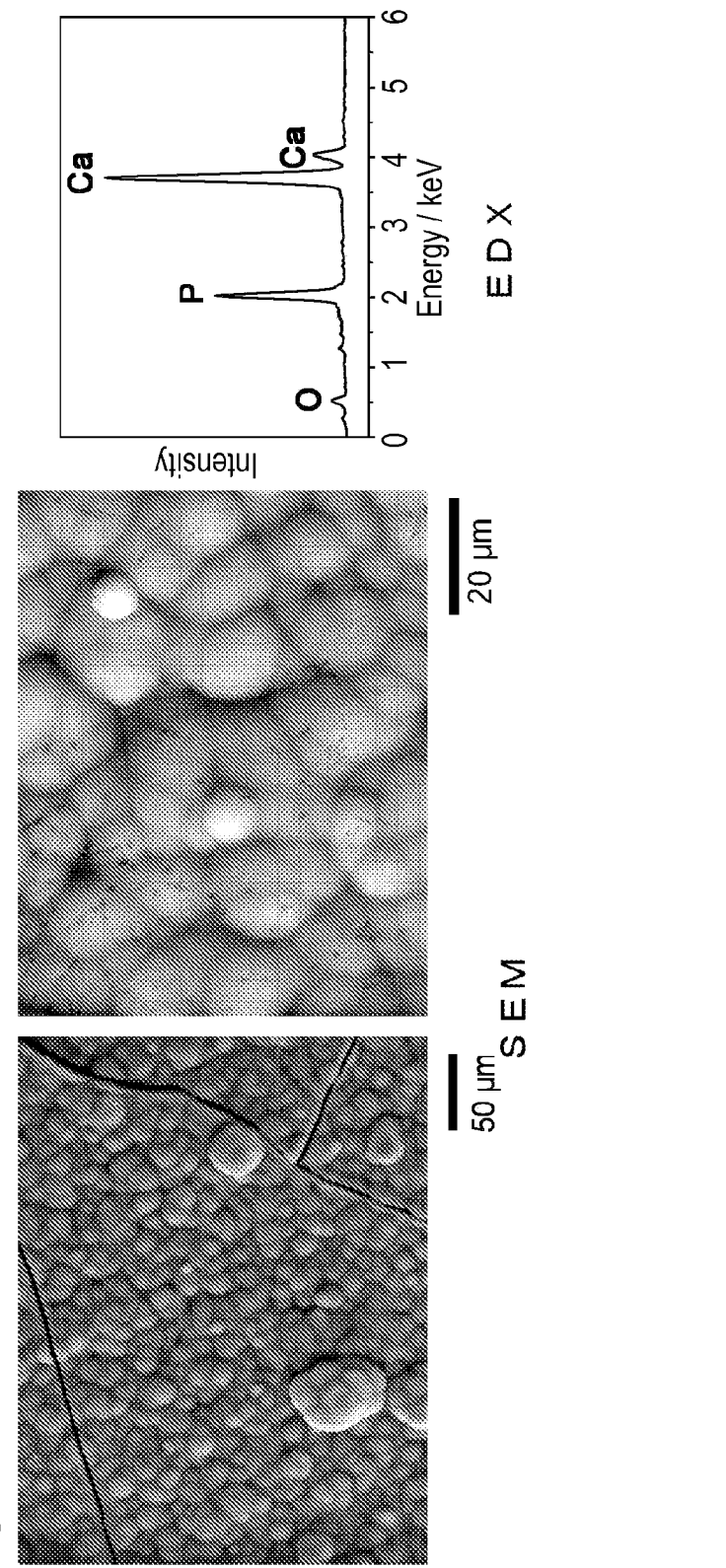
[FIG. 22] It shows the results obtained by SEM and EDX observations of the surface of a substrate subjected to a treatment for imparting bioactivity (Sample M) and which has been left for 14 days after immersion in 1.0SBF in Example 20.

A 10 mm length×10 mm width×1 mm thickness titanium flat plate (manufactured by KOBE STEEL, LTD.) was subjected to a surface roughening treatment using a polishing paper (P2000), followed by ultrasonic cleaning in acetone and air drying to use as a porous substrate. The substrate was immersed in 1.0SBF whose pH was controlled to 8.0 by adding therein tris(hydroxymethyl)aminomethane under a liquid temperature of 36.5° C., and was subjected to a pressurizing treatment (392 MPa) for 1 hour by using a cold isostatic pressing apparatus. Subsequently, the temperature was elevated to 60° C., at which temperature the resulting product was allowed to stand still for 24 hours in an incubator set at 60° C. After passage of 24 hours, the substrate was taken out from the 1.0SBF, rinsed lightly with distilled water, and air dried. Then, the substrate to which bioactivity was imparted by applying the treatment above (Sample M) was immersed in 1.0SBF (pH 7.4) at 36.5° C. for 14 days. The results obtained by SEM and EDX observations of the surface of Sample M immersed in 1.0SBF for 14 days are given in FIG. 22. As is shown clearly in FIG. 22, a coating layer containing hydroxyapatites as the major component was found to gradually form and grow on the surface of Sample M by immersion in 1.0SBF. The adhesion strength of the coating layer containing hydroxyapatites as the major component to the substrate was measured on 4 samples according to the method similar to that described in Example 1, and as a result, an average adhesion strength of 1.5 MPa was obtained with a standard deviation of 1.0 MPa.

Example 21

Figure 23:
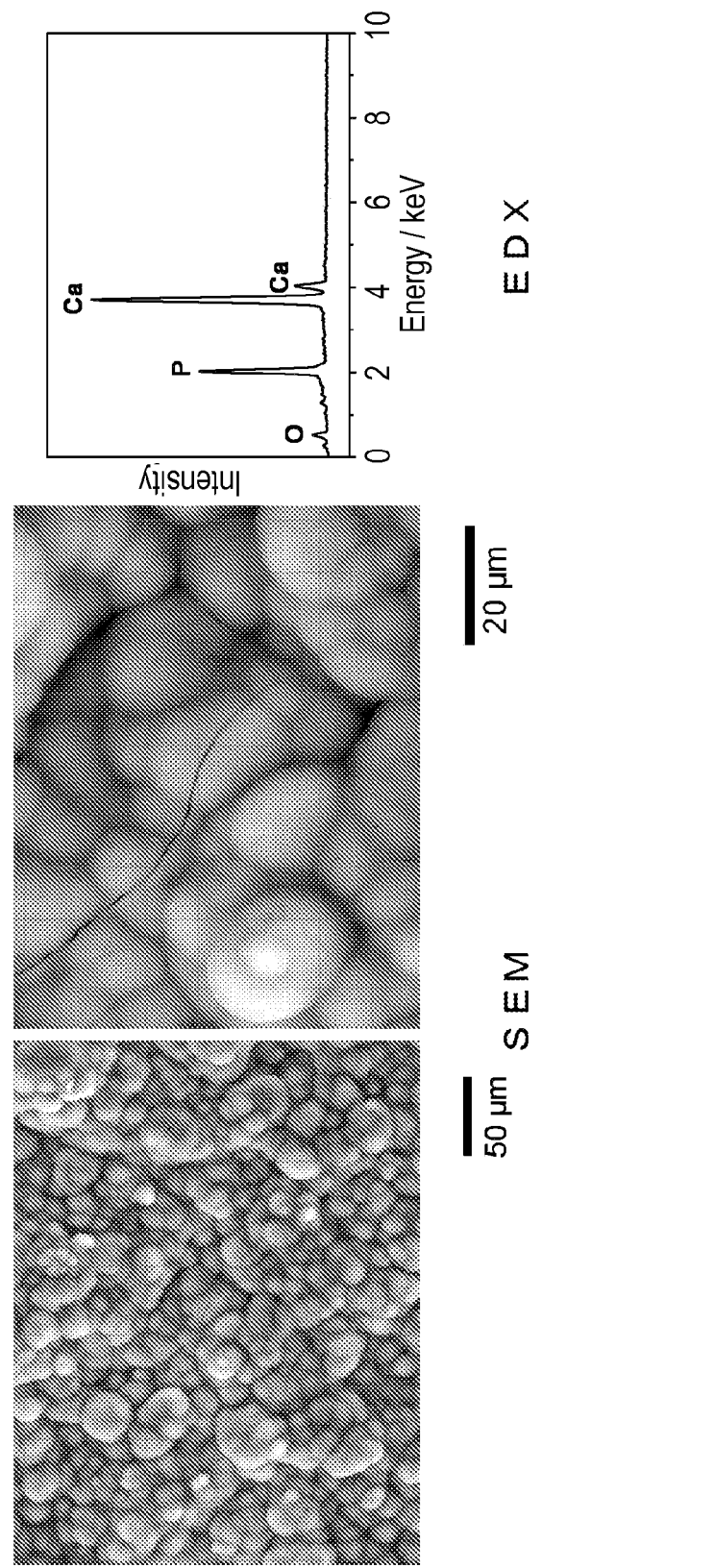
[FIG. 23] It shows the results obtained by SEM and EDX observations of the surface of a substrate subjected to a treatment for imparting bioactivity (Sample N) and which has been left for 14 days after immersion in 1.0SBF in Example 21.

A 10 mm length×10 mm width×1 mm thickness stainless steel flat plate (manufactured by NIPPON METAL INDUSTRY CO., LTD.) was immersed in 18% hydrochloric acid for 24 hours in an incubator set at 60° C., followed by ultrasonic cleaning in distilled water and air drying to use as a porous substrate. The substrate was immersed in 1.0SBF whose pH was controlled to 8.0 by adding therein tris(hydroxymethyl) aminomethane under a liquid temperature of 36.5° C., and was subjected to a pressurizing treatment (392 MPa) for 1 hour by using a cold isostatic pressing apparatus. Subsequently, the temperature was elevated to 60° C., at which temperature the resulting product was allowed to stand still for 24 hours in an incubator set at 60° C. After passage of 24 hours, the substrate was taken out from the 1.0SBF, rinsed lightly with distilled water, and air dried. Then, the substrate to which bioactivity was imparted by applying the treatment above (Sample N) was immersed in 1.0SBF (pH 7.4) at 36.5° C. for 14 days. The results obtained by SEM and EDX observations of the surface of Sample N immersed in 1.0SBF for 14 days are given in FIG. 23. As is shown clearly in FIG. 23, a coating layer containing hydroxyapatites as the major component was found to gradually form and grow on the surface of Sample N by immersion in 1.0SBF. The adhesion strength of the coating layer containing hydroxyapatites as the major component to the substrate was measured on 9 samples according to the method similar to that described in Example 1, and as a result, an average adhesion strength of 2.0 MPa was obtained with a standard deviation of 1.5 MPa.

Example 22

Experiments were conducted under the conditions similar to those used in Example 20, except for using a 10 mm length×10 mm width×1 mm thickness stainless steel flat plate (manufactured by NIPPON METAL INDUSTRY CO., LTD.) as a porous substrate. As a result, it has been found that bioactivity can be imparted to this substrate, and that a coating layer containing hydroxyapatites as the major component can be formed and grown on the surface of the substrate.

Example 23

Figure 24:
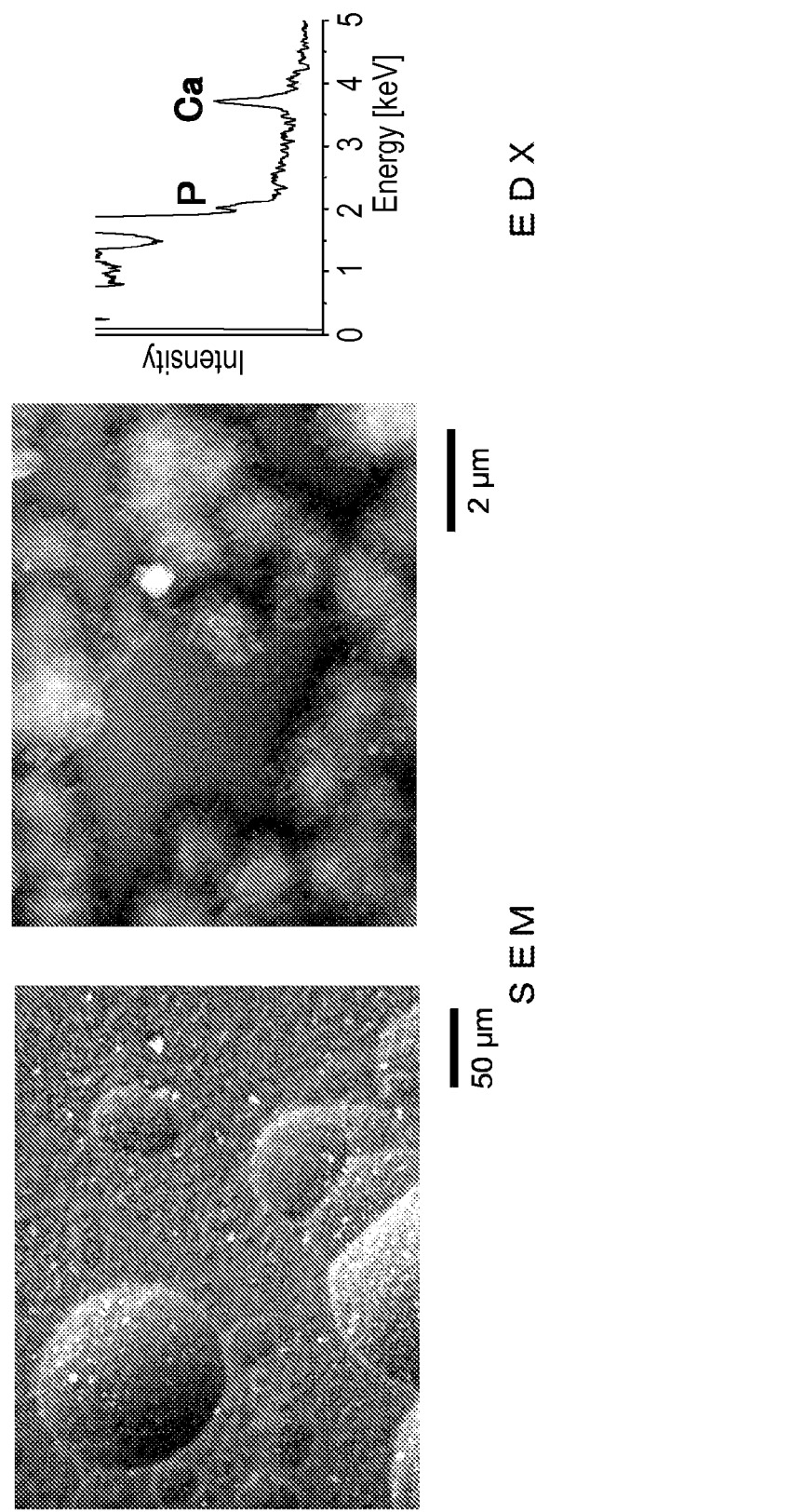
[FIG. 24] It shows the results obtained by SEM and EDX observations of the surface of a substrate subjected to a treatment for imparting bioactivity (Sample O) and which has been left for 3 days after immersion in 1.0SBF in Example 23.

A 10 mm length×10 mm width×1 mm thickness silica glass plate (manufactured by EIKOH Co., Ltd.) was immersed in 46% hydrofluoric acid, allowed to stand still for 12 hours at room temperature, and followed by ultrasonic cleaning in distilled water and air drying to use as a porous substrate. The substrate was immersed in 1.0SBF whose pH was controlled to 8.0 by adding therein tris(hydroxymethyl)aminomethane under a liquid temperature of 36.5° C., and was subjected to a pressurizing treatment (392 MPa) for 1 hour using a cold isostatic pressing apparatus. Subsequently, the temperature was elevated to 60° C., at which temperature the resulting product was allowed to stand still for 24 hours in an incubator set at 60° C. After passage of 24 hours, the substrate was taken out from the 1.0SBF, rinsed lightly with distilled water, and air dried. Then, the substrate to which bioactivity was imparted by applying the treatment above (Sample O) was immersed in 1.0SBF (pH 7.4) at 36.5° C. for 3 days. The results obtained by SEM and EDX observations of the surface of Sample O immersed in 1.0SBF for 3 days are given in FIG. 24. As is shown clearly in FIG. 24, a coating layer containing hydroxyapatites as the major component was found to gradually form and grow on the surface of Sample O by immersion in 1.0SBF.

INDUSTRIAL APPLICABILITY

The present invention has an industrial applicability in the point that it can provide a method for producing bioactive composites having imparted thereto bioactivity, to thereby form and grow in vivo or in vitro a coating layer containing a calcium phosphate compound as the major component with a high adhesion strength on the surface of various types of porous substrates such as a porous shaped body comprising an organic polymer.

The invention claimed is:

1. A method for producing bioactive composites comprising: (1) a step of immersing a porous substrate in a solution containing at least calcium ions and hydrogenphosphate ions, thereby distributing the solution to the inside of at least a part of the pores of the substrate, and then (2) a step of elevating the temperature of the solution by 20° C. or more and/or increasing the pH value of the solution from a pH value in the range of 4.0 to 7.1, to a pH value in the range of 7.2 to 9.0, thereby depositing particles of particle size 1 nm to 500 µm containing a calcium phosphate compound as the major component inside the pores into which the solution is introduced.

2. The production method as claimed in claim 1, wherein the porous substrate is a porous shaped body comprising an organic polymer.

3. The production method as claimed in claim 1, wherein the average diameter of the pores is in the range of 10 nm to 1 mm.

4. The production method as claimed in claim 1, wherein the porosity of the porous substrate is in the range of 10% to 65%.

5. The production method as claimed in claim 2, wherein the organic polymer is at least one type selected from polyethylene, polypropylene, polyethylene terephthalate, polyvinyl alcohol, ethylene-vinyl alcohol copolymer, polyethersulfone, polycaprolactone, and polylactic acid.

6. The production method as claimed in claim 1, wherein the calcium phosphate compound is hydroxyapatites.

7. The production method as claimed in claim 1, wherein in the step (1), a degassing treatment is carried out to thereby distribute the solution to the inside of at least a part of the pores of the substrate.

8. The production method as claimed in claim 1, wherein in the step (1), a pressurizing treatment is carried out to thereby distribute the solution to the inside of at least a part of the pores of the substrate.

9. The production method as claimed in claim 1, wherein the pH value of the solution is increased by adding a pH controlling agent having a buffer function.

10. The production method as claimed in claim 9, wherein the pH controlling agent having a buffer function is tris(hydroxymethyl)aminomethane.

11. The production method as claimed in claim 1, wherein a plasma surface treatment is applied to the porous substrate before carrying out the step (1).

12. The production method as claimed in claim 1, wherein the porous substrate is subjected to a surface roughening treatment to provide poriform irregularities to the surface thereof.

13. A method for producing bioactive composites having on the surface thereof a coating layer containing a calcium phosphate compound as the major component, comprising: (1) a step of immersing a porous substrate in a solution containing at least calcium ions and hydrogenphosphate ions, thereby distributing the solution to the inside of at least a part of the pores of the substrate, then (2) a step of elevating the temperature of the solution by 20° C. or more and/or increasing the pH value of the solution from a pH value in the range of 4.0 to 7.1, to a pH value in the range of 7.2 to 9.0, thereby depositing particles of particle size 1 nm to 500 μm containing a calcium phosphate compound as the major component inside the pores into which the solution is introduced, and (3) a step of forming and growing a coating layer containing a calcium phosphate compound as the major component by using the particles containing a calcium phosphate compound as the major component, which have deposited inside the pores, as nuclei.

* * * * *